(12) United States Patent
Ritschel et al.

(10) Patent No.: US 6,365,185 B1
(45) Date of Patent: Apr. 2, 2002

(54) SELF-DESTRUCTING, CONTROLLED RELEASE PERORAL DRUG DELIVERY SYSTEM

(75) Inventors: Wolfgang A. Ritschel, Cincinnati; Mukul A. Agrawal, Strongsville, both of OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/277,258

(22) Filed: Mar. 26, 1999

Related U.S. Application Data

(60) Provisional application No. 60/079,403, filed on Mar. 26, 1998.

(51) Int. Cl.$^7$ .............................. A61K 9/24; A61K 9/20; A61K 9/26; A61K 9/22

(52) U.S. Cl. ...................... 424/473; 424/464; 424/465; 424/466; 424/468; 424/469; 424/470; 424/471; 424/472

(58) Field of Search ............................ 424/400, 408, 424/409, 463, 464, 465, 468, 471, 472, 473, 466, 469, 470

(56) References Cited

U.S. PATENT DOCUMENTS

| | | | | |
|---|---|---|---|---|
| 4,673,405 A | * | 6/1987 | Guittard et al. | 604/890 |
| 5,531,736 A | * | 7/1996 | Wong et al. | 604/892.1 |
| 5,580,979 A | * | 12/1996 | Bachovchin | 540/509 |
| 5,607,697 A | * | 3/1997 | Alkire et al. | 424/495 |
| 5,681,583 A | * | 10/1997 | Conte et al. | 424/472 |
| 5,707,654 A | * | 1/1998 | Beres et al. | 424/466 |
| 5,780,055 A | * | 7/1998 | Habib et al. | 424/464 |
| 5,824,339 A | * | 10/1998 | Shimizu et al. | 424/466 |

OTHER PUBLICATIONS

M.A. Agrawal and W.A. Ritschel, Evaluation of a New Peroral Modified Release System in Human Subjects (abstract), aaps American Association of Pharmaceutical Scientists, 1977.

David R. Swanson, Ph.D. et al., Nifedipine Gastrointestinal Therapeutic System, The American Journal of Medicine, vol. 83 (suppl 6B), Dec. 21, 1987.

W.A. Ritschel, A. Sabouni, and MA Agrawal, Novel p.o. drug delivery system: Compression–coated hydrogel piston pump. 1. Shell thickness and pore size., Pharmaceutical and Pharmacological Letters, vol. 6, No. 3, Dec. 1996.

W.A. Ritschel, A. Sabouni, and M.A. Agrawal, Novel p.o. drug delivery system: Compression–coated hyudrogel piston pump. 2. Design and in vitro evalution, Pharmaceutical and Pharmacological Letters, vol. 6, No. 3, Dec. 1996.

W.A. Ritschel et al., Permeability of [3H]Water Across a Porous Polymer Matrix used as Rate–Limiting Shell in Compression–coated Tablets, Journal of Controlled Release, 12 (1990) 97–102.

Bengt Lindstedt et al., Osmotic pumping release from KCl tablets coated with porous and non–porous ethylcellulose, International Journal of Pharmaceutics, 67 (1991) 21–27.

WA Ritschel, Biopharmaceutic and Pharmacokinetic Aspects in the Design of Controlled Release Peroral Drug Delivery Systems, Drug Development and Industrial Pharmacy, 15(6&7), 1073–1103 (1989).

Gaylen M. Zentner et al., Osmotic Flow Through Controlled Porosity Films: An Approach To Delivery Of Water Soluble Compounds, Journal of Controlled Release, 2 (1985) 217–229.

Wolfgang A. Ritschel et al., Evaluation of a Controlled Release Osmotic Pump Type of Dosage Form for Chlorpheniramine Maleate, Eur. J. Pharm. Biopharm. 40(3) 122–127 (1994).

* cited by examiner

Primary Examiner—Thurman K. Page
Assistant Examiner—S. Tran
(74) Attorney, Agent, or Firm—Wood, Herron & Evans, LLP

(57) ABSTRACT

The present invention relates to tablets which are time-controlled to release active agent at different rates in different regions of the digestive tract in order to maintain a substantially constant concentration in the blood. In one embodiment, a new modified release drug delivery system, for once a day peroral use, consisting of a solid core comprising an active agent together with a hydrogel, with the solid core being coated with a semi-permeable, self-destructing membrane which is optionally drilled to provide a release orifice, and then optionally further coated with the same or different active agent material. The device delivers the active agent in a substantially constant effective dose for the duration of the transit through the stomach and small intestine, followed by accelerated release when reaching the large intestine.

67 Claims, 15 Drawing Sheets

SELF-DESTRUCTING, CONTROLLED RELEASE PERORAL DRUG DELIVERY SYSTEM

CROSS-REFERENCE TO RELATED APPLICATION

This Application claims the benefit of the filing date of Provisional U.S. Patent Application No. 60/079,403 entitled "Self-Destructing Controlled Release Peroral Drug Delivery System" and filed on Mar. 26, 1998.

BACKGROUND OF THE INVENTION

1. Field of the Invention

The present invention relates to tablets which are time-controlled controlled to release active agent at different rates in different regions of the digestive tract in order to maintain a substantially constant concentration in the blood.

2. Description of the Related Art

The development of novel peroral drug delivery systems for achieving controlled administration of the active agent with minimum dependability on drug and environmental properties, has attracted a great deal of interest. Among the first systems designed and marketed successfully was the elementary osmotic pump. This system consists of a compacted core coated with a microporous, semipermeable membrane having a delivery orifice drilled in the coating by LASER. The core tablet consists of either an osmotically active therapeutic compound or a mixture of an osmotically active agent and the therapeutic compound. The osmotic pump imbibes water, dissolving the drug in the core and the drug solution is delivered through the delivery orifice at steady state and at a rate controlled by the rate of influx of the water across the semipermeable membrane.

The delivery devices described above operate successfully for their intended use and they can deliver many beneficial agents for their intended effects. Now, it has been observed their use can be limited because they lack the necessary elements to deliver beneficial agents at the appropriate amounts for the environments encountered in the gastrointestinal tract.

It will be appreciated by those versed in the dispensing arts that if a delivery system is provided for administering at a controlled rate throughout the entire gastrointestinal tract, the different absorptive rates of the various sections of the tract will result in a change in the blood levels of the delivered compound.

SUMMARY OF THE INVENTION

The goal of the present invention is to design a system or device which contains, instead of an osmotically active agent, a dry swelling material and instead of a semipermeable membrane by spray-or dip-coating, a semipermeable shell by press-coating and an exit means through which the drug solution is expelled at a predetermined rate over a period of 8 or 14 hours for a 12 or 24 hours duration of effect. The exit means may be a delivery orifice which can be made by a stylus in the upper punch of the compression tools. The advantage of the present system is the adaptability to manufacturing on a compression coating machine, in one single step.

Once the delivery system of the present invention reaches the large intestine, where absorption of drug is slower because of mucosal viscosity of the intestinal contents, the shell of the device self-destructs destructs thus releasing the drug at an accelerated rate.

It is accordingly an object of the present invention to provide a delivery device for the oral administration of a pharmaceutically acceptable active agent to a warm-blooded animal, with increasing delivery rate, particularly to the lower portion of the small intestine and/or the colon, more particularly to the colon.

It is another object of this invention to provide a dosage form for delivering substantially all of a therapeutic drug to the colon.

It is yet another object of this invention to provide a dosage form which comprises a core tablet coated with a delay jacket for delaying the delivery of the drug to insure the time required for the dosage form to travel through the small intestine.

These, and other objects apparent to those skilled in the art from the following detailed description, are accomplished by the present invention which pertains to the delivery of a therapeutic drug to a pre-selected region of the gastrointestinal tract, by means of a drug delivery device. This drug delivery device comprises:

BRIEF DESCRIPTION OF THE DRAWINGS

In the drawings, which are not drawn to scale, but are set forth to illustrate various embodiments of the invention, the drawing figures are as follows.

DETAILED DESCRIPTION OF THE DRAWINGS

The disclosure of Provisional U.S. Patent Application No. 60/079,403, entitled "Self-Destructing Controlled Release Peroral Drug Delivery System": and filed on Mar. 26, 1998, is incorporated herein in its entirety by reference.

This invention pertains to a drug delivery device for the oral administration of a pharmaceutically acceptable active agent to a warm-blooded animal, including humans. The device delivers a compound in a sustained manner to the upper portion of the gastrointestinal tract and then a greater burst of release at the lower small intestine and the colon, more particularly to the colon.

Figure 1:
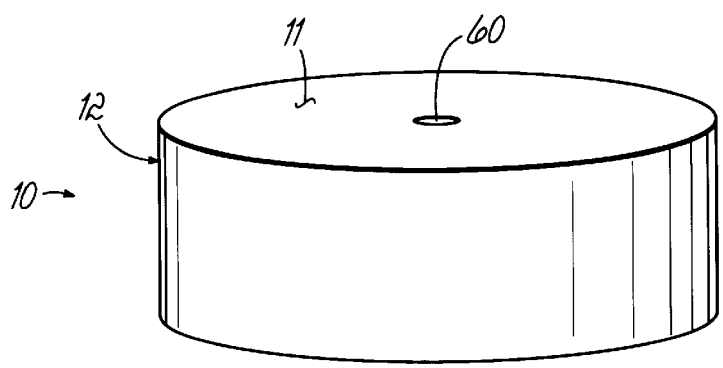
FIG. 1 is a view of an osmotic-pump dispensing system designed for orally administering a beneficial agent such as a drug to the gastrointestinal tract in varying delivery rates.

An osmotic-pump delivery system is seen in FIG. 1, identified by the numeral 10. In FIG. 1, delivery system 10 is designed as an orally administrable drug delivery device, and it comprises a body member 11, a wall 12, and at least one passageway 60 in wall 12.

Figure 2:
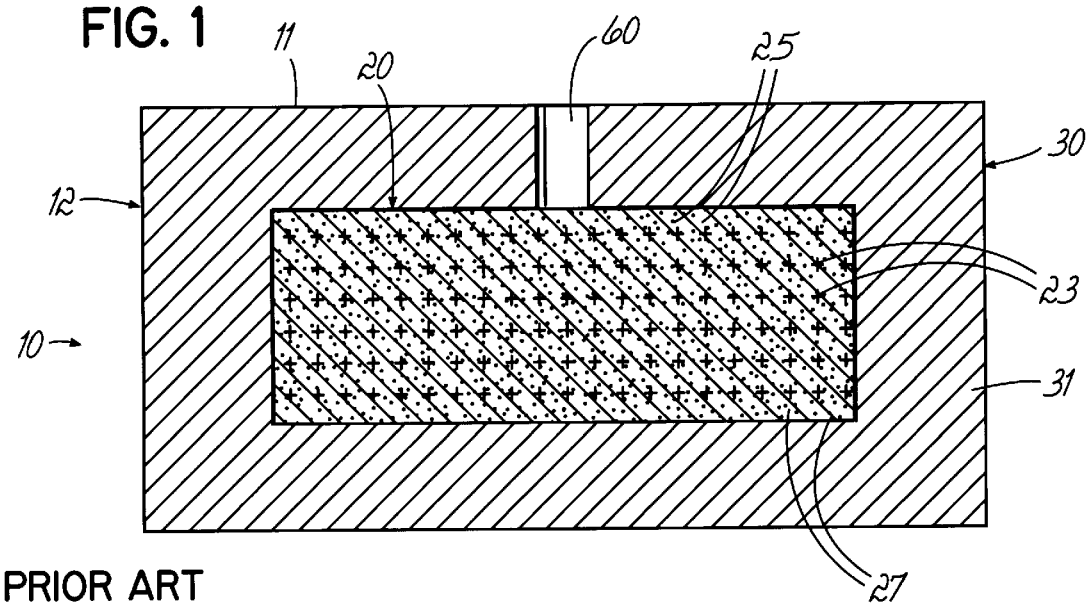
FIG. 2 is a side cutaway view of the osmotic-pump dispensing system of FIG. 1, including a semi-permeable wall and release orifice.

FIG. 2 depicts the osmotic-pump drug delivery system 10 in a cross-sectional view for illustrating the structural members of the delivery system 10. In FIG. 2, system 10 comprises body 11, wall 12, passageway 60 and internal compartment or compartment 20. Passageway 60 extends through wall 12 and it connects internal compartment 20 with the exterior of system 10. Wall 12 of the delivery system illustrated in FIG. 2 comprises a matrix 31 which comprises a semi-permeable composition that is permeable to the passage of an external fluid present in the environment of use, and it is essentially impermeable to the passage of an active agent such as a drug. Matrix 31 is substantially inert, it maintains its physical and its chemical integrity during the dispensing of a beneficial drug, and it is non-toxic to animals, including humans. Matrix 31 may be in laminar arrangement with other composites.

With regard to FIG. 2, compartment 20 contains a beneficial agent 23, represented by "plus signs", that is soluble to very soluble in an external fluid imbibed into compartment 20. In the preferred embodiment, the beneficial agent 23 mixes with external fluid, indicated by diagonal dashes, which passes through the composite wall 12 and is imbibed into compartment 20.

In another embodiment of the osmotic-pump delivery device, compartment 20 contains a beneficial agent 23 that has limited solubility in fluid 25 imbibed into compartment 20, and in this instance it exhibits a limited osmotic pressure gradient across wall 12, mainly semipermeable composite 30 against the external fluid 25. In this latter embodiment, beneficial agent 23 optionally is mixed with an osmotic agent 27, indicated by dots, that is soluble in the external fluid and it exhibits an osmotic pressure gradient across wall 12 against an external fluid.

Figure 3:
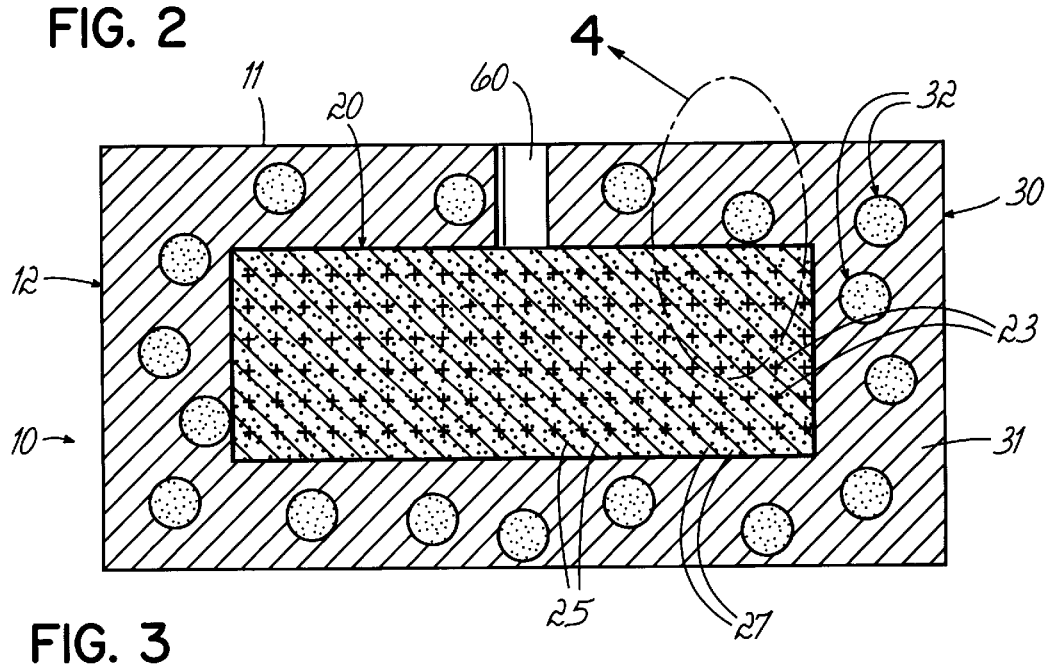
FIG. 3 is a side cutaway view of an embodiment of the dispensing system in accordance with the principles of the present invention, with the embodiment including a self-destructing wall, and which system is useful for delivering a beneficial agent to the digestive tract.

Turning now to drawing FIGS. 3–17, which drawing figures are examples of various aspects and embodiments of delivery systems made in accordance with the principles of the invention, and which are not to be construed as limiting, one example of a delivery system is seen in FIG. 3 as identified by the number 10. FIG. 3 depicts the self-destructing drug delivery system 10 provided by the present invention. In FIG. 3, system 10 is seen in opened section with a portion of wall 12 removed at 21. In FIG. 3, system 10 comprises body 11, wall 12, passageway 60, and internal compartment 20. Wall 12 of the delivery system illustrated in FIG. 3 comprises a composite formed essentially of a semipermeable matrix 31, that is permeable to the passage of an external fluid and it is essentially impermeable to the passage of active agent 23, and a multiplicity of embedded disintegrants 32. Disintegrants 32 comprise a swelling agent 34 which is coated by a delay jacket 33. Compartment 20 of delivery device 10 shown in FIG. 3 comprises a beneficial agent 23, and, optionally, an osmotically effective compound 27. During operation, when the delivery system 10 is in the environment of use dispensing beneficial agent 23, compartment 20 contains also imbibed external fluid 25. Generally, wall 12 is a semipermeable composite having a wall thickness of from about 25 microns to about 800 microns.

Figure 4:
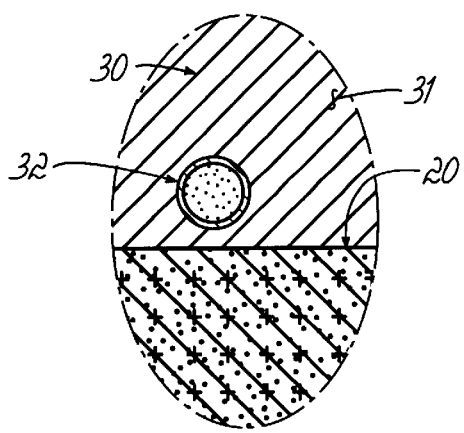
FIG. 4 illustrates an enlarged view of the composite defining the structural member of the system taken through 4—4 of FIG. 3 and shows a disintegrant embedded in the wall of the system.

FIG. 4 illustrates a view taken through 4—4 of FIG. 3. FIG. 4 depicts wall 12 comprising a composite 30 made up of matrix 31 having homogeneously or heterogeneously (i.e., evenly or unevenly distributed) disintegrants 32 dispersed throughout matrix 31.

Figure 5:
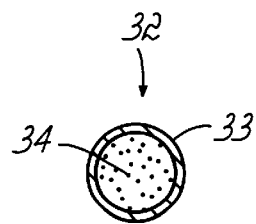
FIG. 5 illustrates a cutaway view of the coated disintegrant of the device of FIGS. 3 and 4.

FIG. 5 illustrates a cross-sectional view of a disintegrant 32. Disintegrant 32 comprises a swelling agent 34 which is generally any material which swells or increases in volume upon contact with imbibed fluid. Swelling agent 34 is preferably coated by a delay jacket 33 in a coating thickness which delays.

Figure 6:
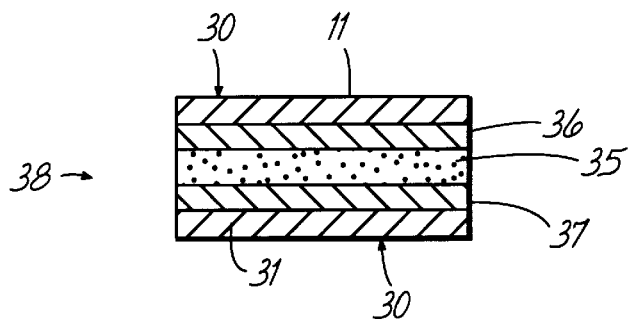
FIG. 6 depicts a side cutaway view of another embodiment of the composite defining the self-destructing membrane of a version of the dispensing system taken through 4—4 of FIG. 3, and illustrates another embodiment of the invention comprising a laminate of disintegrant, inner and outer coatings, and membrane wall.

FIG. 6 illustrates a view taken through 4—4 of FIG. 3. FIG. 6 depicts an alternate embodiment of wall 12 comprising a laminate 38 made up of an osmotic agent lamina 35 in contact with an inner delay jacket lamina 37 and outer delay jacket lamina 36. The inner and outer delay jacket lamina are then in contact with a matrix lamina 30.

Figure 7:
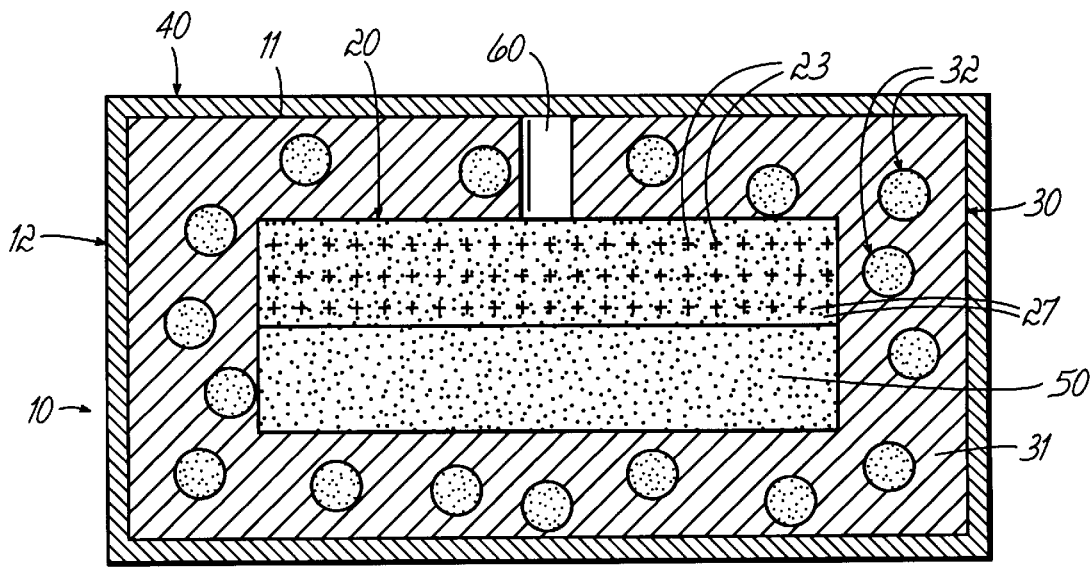
FIG. 7 depicts a side cutaway view of a further embodiment of the dispensing system in accordance with the principles of the invention, comprising a self-destructing wall, an active agent core, a push means, and a delay jacket, and which system is useful for delivering a beneficial agent to the digestive tract.

FIG. 7 depicts the self-destructing osmotic system 10 provided by the invention. In FIG. 7, system 10 is seen in opened section with a portion of wall 12 removed at 21. In FIG. 7, system 10 comprises body 11, wall 12, orifice 60, and internal compartment 20. Wall 12 of the delivery system illustrated in FIG. 7 comprises a composite formed essentially of a semipermeable matrix 31, that is permeable to the passage of an external fluid and it is essentially impermeable to the passage of active agent 23, and a multiplicity of embedded disintegrants 32. Disintegrants 32 comprises a swelling agent 34 which is coated by a delay jacket 33. Compartment 20 of delivery device 10 shown in FIG. 7 comprises a beneficial agent 23, and, optionally, an osmotically effective compound 27. During operation, when the delivery system 10 is in the environment of use dispensing beneficial agent 23, compartment 20 contains also imbibed external fluid 25. Generally, wall 12 is a semipermeable composite having a wall thickness of 25 to 800 microns. FIG. 7 shows an optional push means 50 which, upon contact with imbibed fluid, consumes volume inside the core compartment by swelling and thereby pushes the active agent formulation through the exit means. FIG. 7 also depicts an optional delay jacket 40 which may be coated over the composite matrix 31 and is formed of an enteric material that does not dissolve or disintegrate in the stomach during the time the delivery system remains in the stomach, and the enteric material should disintegrate once the delivery system enters the small intestine.

Figure 8:
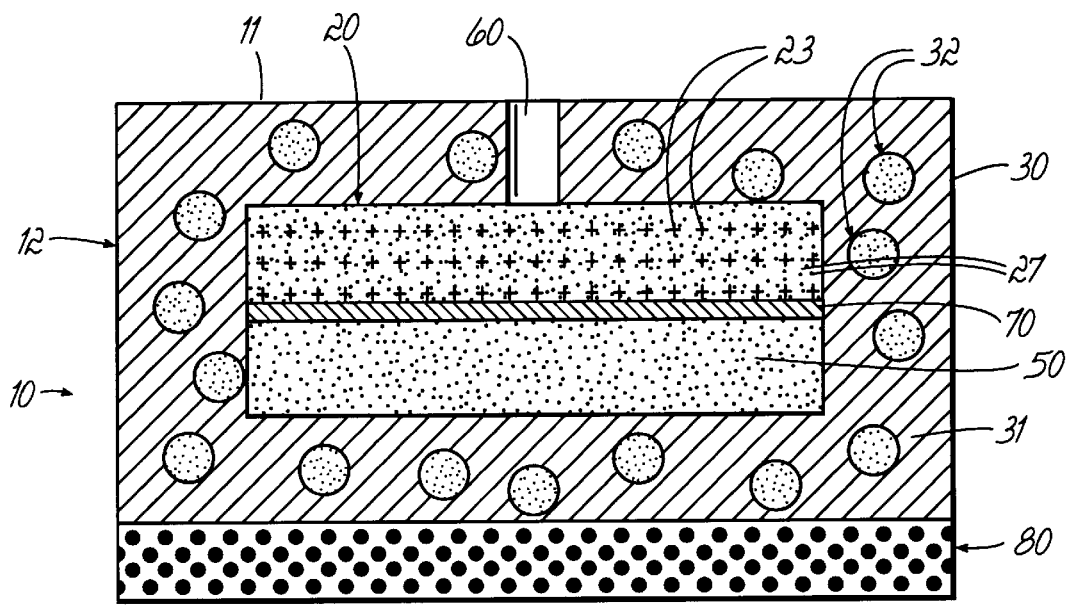
FIG. 8 depicts a side cutaway view of yet another embodiment of the dispensing system in accordance with the principle of the invention, comprising a piston pump device with a self-destructing wall, an active agent core, a push means, an initial release layer, and a piston diaphragm between the swelling agent and active agent core and which system is useful for delivering a beneficial agent to the digestive tract.

FIG. 8 depicts the self-destructing drug delivery system 10 provided by the invention. In FIG. 8, system 10 is seen in opened section with a portion of wall 12 removed at 21. In FIG. 8, system 10 comprises body 11, wall 12, exit means 60, and internal compartment 20. Wall 12 of the delivery system illustrated in FIG. 8 comprises a composite having a semipermeable matrix 31 that is permeable to the passage of an external fluid and it is essentially impermeable to the passage of active agent 23, and a multiplicity of embedded disintegrants 32. Disintegrants 32 comprises an swelling agent 34 which is coated by a delay jacket 33. Compartment 20 of delivery device 10 shown in FIG. 8 comprises a beneficial agent 23, and, optionally, an osmotically effective compound 27. During operation, when the delivery system 10 is in the environment of use dispensing beneficial agent 23, delivery compartment 20 contains also imbibed external fluid 25. Generally, wall 12 is a semipermeable composite having a wall thickness of 25 to 800 microns. FIG. 8 shows an optional push means 50 which is separated from the active agent formulation by a diaphragm 70.

Delivery system 10 shown in FIGS. 3 through 8 can be made into many embodiments for oral use for releasing locally or systemically acting therapeutic medicaments throughout the gastrointestinal tract. The delivery system may be designed so that delivery is intermittently or in a predetermined section of the gastrointestinal tract. The oral system can have various conventional shapes and sizes such as round with a diameter of ⅛ inch to ⁹⁄₁₆ inch, or it can be shaped like a capsule having a range of sizes from triple zero to zero and from 1 to 8. In these manufactures, system 10 can be adapted for administering a beneficial agent to warm-blooded mammals such as humans. It is to be understood the delivery systems shown are not to be construed as limiting, as the delivery systems can take a wide variety of shapes, sizes and forms adapted for delivering beneficial agents to environments of use.

The modified release drug delivery system 10 of the present invention is designed for once a day peroral use, consisting of a solid core comprising an active agent 23 and optionally together with an osmotic agent 27. The core compartment 20 is coated with a semi-permeable, self-destructing shell 30 which is optionally drilled, formed or punched to provide a release passageway 60, and then optionally further coated with the same or different active agent material 80 which provides an initial dosing phase. The device delivers the active agent in a substantially constant effective dose for the duration of the gastrointestinal transit.

Previous sustained-release, drug delivery devices have a 0, $1^{st}$, √t (square root of time), or pulsatile release pattern. The delivery device of the present invention now offers a multiphase delivery profile. The delivery device of the present invention provides a physiologically-based, varying release pattern where, if desired, there is a constant delivery to the stomach and small intestine and then an accelerated increase of release in the large intestine where absorption is lower and a greater concentration gradient is necessary to maintain the same drug concentration in the host's blood.

The drug delivery device of the present invention comprises:

a core compartment comprising a bioavailable and biocompatible beneficial agent formulation and a means for delivering the agent formulation from the delivery system; and a self-destructing housing.

Optionally, the device may further comprise one or more of the following:

a delay jacket;

an expandable, volume consuming, driving member;

an osmotic agent;

one or more additional core excipients;

an exit means;

a diaphragm or partition; and one or more additional coatings.

FIG. 9 depicts the drug release profile from the self-destructing delivery system of the present invention as it compares to the change in gastrointestinal physiology over the course of time.

Figure 9A:
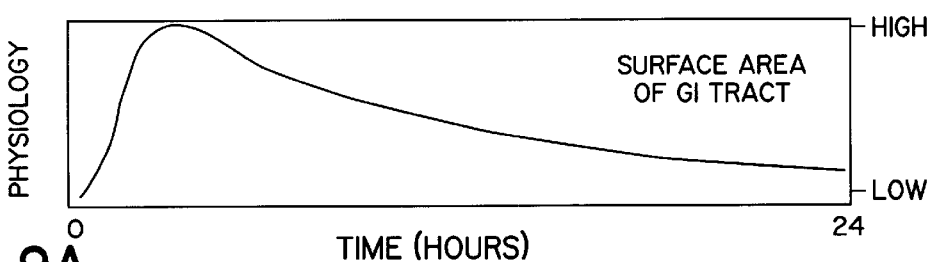
FIG. 9 depicts the drug release profile from the self-destructing delivery system of the present invention as it compares to the change in gastrointestinal physiology over the course of time.

In FIG. 9a, the graph shows that the surface area of the gastrointestinal tract changes from low to high and then gradually back to low as the delivery device travels through the tract over time. A lower surface area will result in a lower transfer of delivered drug from the tract into the bloodstream.

Figure 9B:
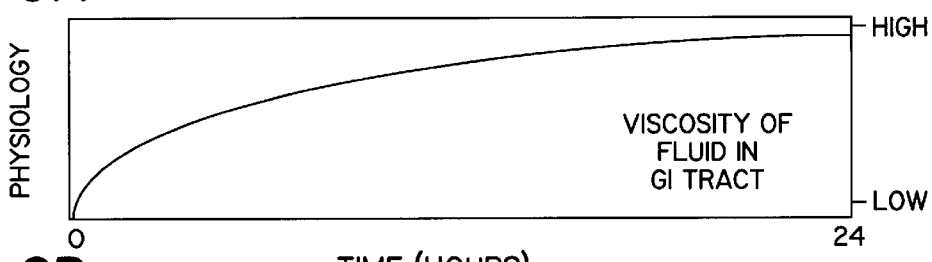

In FIG. 9b, the graph shows that the viscosity of the fluid inside of the gastrointestinal tract changes from low to high as the delivery device travels through the tract over time. The transfer of delivered drug from the tract into the bloodstream is highest when the viscosity is the lowest.

Figure 9C:
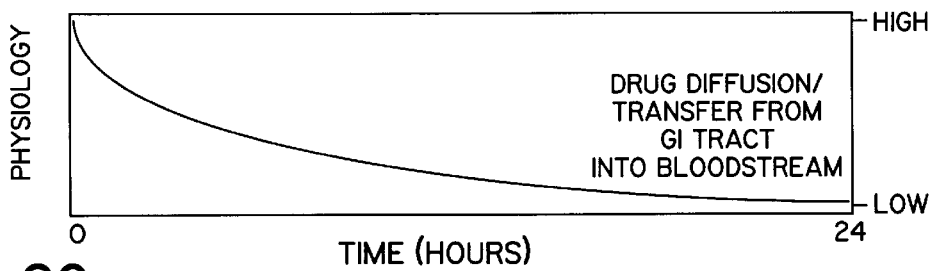

In FIG. 9c, the graph shows the diffusion or transfer of delivered drug from the tract into the bloodstream as the delivery device travels through the tract over time.

Figure 9D:
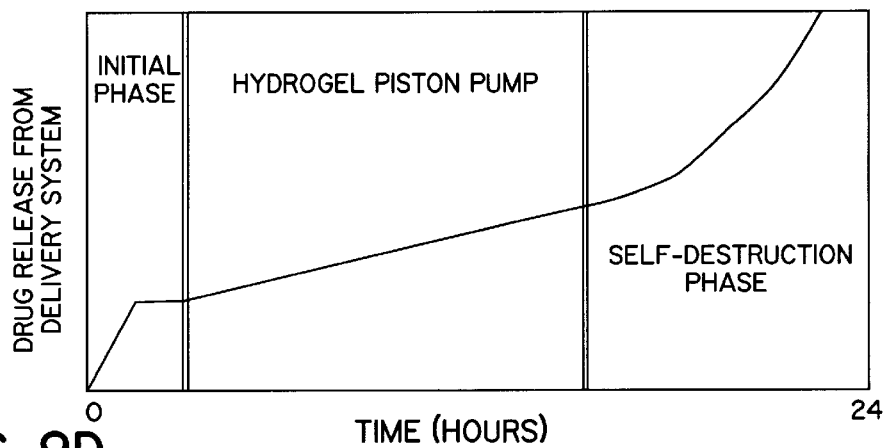

In FIG. 9d, the graph shows that the amount of drug released from the device inside of the gastrointestinal tract changes from low to high as the delivery device travels through the tract over time. The drug release profile shows an initial burst of release from an optional initial release layer, a second profile of slowly increasing release as the device travels through the small intestine and a third profile showing the self-destructing phase where release is greatest as the device travels through the large intestine and colon.

Figure 9E:
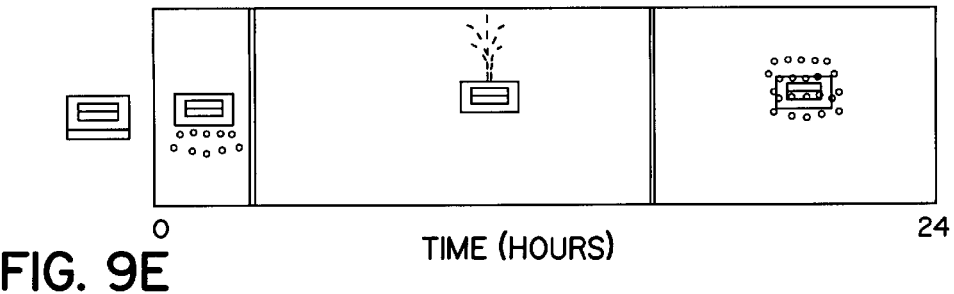

FIG. 9e shows a depiction of the device as the delivery method changes as the device passes through the different portions of the tract with the highest delivery to the large intestine and colon.

a. Core Compartment

Compartment 20 comprises a beneficial agent formulation (also known as an active agent formulation), which beneficial agent formulation comprises a beneficial agent (also referred to as an active agent) and, optionally, a pharmaceutically acceptable carrier. If desired, the pharmaceutically acceptable carrier may comprise a buffer, a pharmaceutically acceptable, viscosity-modulating vehicle, a pharmaceutically acceptable surfactant, and/or other formulation ingredients. The core comprises an active agent formulation 23 and may optionally include other pharmaceutically acceptable excipients including osmotic agents, lubricants, glidants, wetting agents, binders, fillers, and suspending/thickening agents.

Active agents useful in the present invention include, but are not limited to, proteins and peptides, antiasthmatics, antianginals, corticosteroids, 5-lipoxygenase inhibitors, antihypertensives, and leukotriene B4 receptor antagonists. Proteins and peptides include, but are not limited to, transforming growth factors (TGF), immunoglobulin E (IgE) binding factors, interleukins, interferons (IFN), insulin-like growth factors (IGF), milk growth factors, anticoagulants, and parathyroid hormones (PTH). Virtually any other active agent which is known to be intestinally and colonically absorbable or used to topically treat the intestines and colon can be used as an active agent in the present invention as long as it is compatible with the system components. Generally, the delivery system 10 comprises from about 5 nanograms to 20 grams of beneficial agent.

Compartment 20 generally comprises a beneficial agent 23 and optionally contains one or more components selected from the group consisting of a pharmaceutically acceptable, viscosity-modulating vehicle, a buffer, and a surfactant. The pharmaceutically acceptable, viscosity-modulating vehicle in one embodiment comprises a polyol such as a diol, triol, polyhydric alcohol, or the like.

More specific polyols comprise 1,5-pentylene glycol; 1,6-hexylene glycol; 1,7-heptylene glycol; 1,9-nonylene glycol; 1,2-dimethyl-1,6-hexylene glycol; 1,2,3-propanetriol; 1,2,5-pentanetriol; 1,3,5-pentanetriol; 1,2,4-butanetriol; dipentaerythriol, and the like. In another embodiment the pharmaceutically acceptable, viscosity-mudulating vehicle comprises glycerol mono(lower alkyl) ethers and glycerol di(lower alkyl) ethers such as glycerol 1-methyl ether; glycerol 1-ethyl ether; glycerol 1,2-dimethyl ether; glycerol 1,3-dimethyl ether, and the like. In another embodiment the pharmaceutically acceptable, viscosity-modulating vehicle comprises a mixture such as propylene glycol and glycerol; a mixture comprising propylene glycol, ethanol and glycerol, or the like. The pharmaceutically acceptable vehicle functions as a viscosity-modulating means for the components present in a compartment 20, as a vehicle for transporting beneficial agent 23 from compartment 20, it provides protection against the decomposition of a beneficial agent, and it imparts physical chemical stability to components present in compartment 20. The viscosity-modulating vehicle may be used to increase the viscosity of the formulation to prevent mixing fluids (e.g., gastric or intestinal fluid) in the implantation environment from mixing with the beneficial agent carried in formulation within compartment 20. The pharmaceutically acceptable, viscosity-modulating vehicle is present in the compartment 20 in an amount of about 0.1% to 90% by weight.

Representative pharmaceutically acceptable buffers in compartment 20 that are blended with the beneficial agent 34 and the pharmaceutically acceptable fluid comprise non-toxic buffers and solutions thereof, solutions that resist change of pH thereby giving stability to the components present in compartment 20. In another embodiment the buffer and solutions thereof can be used alone and, in a presently preferred embodiment, the buffer and solution thereof is used in combination with the pharmaceutically and pharmacologically acceptable aqueous miscible fluids (e.g., gastric or intestinal fluids). Typical buffer aqueous solutions comprise sodium dihydrogen phosphate (0.025M) and disodium monohydrogen phosphate (0.025M); sodium dihydrogen phosphate (0.025M), disodium monohydrogen phosphate (0.025M) and sodium chloride (0.15M); sodium carbonate (0.025M), sodium monohydrogen carbonate (0.025M) and sodium chloride (0.15M); potassium dihydrogen phosphate (0.025M) and sodium monohydrogen phosphate (0.025M); potassium dihydrogen phosphate (0.0087M) and sodium monohydrogen phosphate (0.0302M); potassium hydrogen tartrate (0.034M) and potassium dihydrogen phosphate (0.025M); acetic acid (0.1M) and sodium acetate (0.1M), and the like. The buffers comprise also citric acid and sodium hydroxide; potassium hydrogen phthalate and sodium hydroxide; potassium hydrogen phosphate and sodium phosphate; tris (hydroxymethyl)aminomethane and hydrochloric acid; sodium tetraborate and hydrochloric acid; glycine and hydrochloric acid; triethanolamine and hydrochloric acid; N-tris (hydroxymethyl)methyl-2-amino sulfonic acid and sodium hydroxide, and the like. The buffer aqueous solution in another embodiment can comprise a component such as sodium phosphate monobasic, sodium phosphate dibasic, potassium hydrogen tartrate, potassium dihydrogen citrate, potassium hydrogen phthalate, sodium tetraborate, sodium carbonate sodium hydrogen carbonate, and the like, or combinations thereof.

Representative pharmaceutically acceptable surfactants for the present purpose comprise anionic, cationic, amphoteric and nonionic surfactants. More specific examples of surfactants comprise sorbitan trioleate, sorbitan tristearate, propylene glycol monostearate; sorbitan sesquiolate; glycerol monostearate; sorbitan monooleate; propylene glycol monolaurate; sorbitan monostearate; diethylene glycol monostearate; glycerol monostearate; diethylmonolaurate; sorbitan monopalmitate; sorbitan monolaurate; polyoxyethylene lauryl ether; polyoxyethylene sorbitan monostearate; polyoxyethylene sorbitan monooleate; polyoxyethylene sorbitan tristearate; polyoxyethylene sorbitan trioleate; polyoxyethylene glycol monooleate; polyoxyethylene glycol monostearate; triethanolamine oleate; polyoxyethylene monyl phenol; polyethylene glycol monolaurate; polyoxyethylene sorbitan monolaurate; polyoxyethylene sorbitan monostearate; polyoxyethylene sorbitan monooleate; polyoxyethylene stearyl ether; polyoxyethylene oleyl ether; polyoxyethylene sorbitan monopalmitate; polyoxyethylene cetyl ether; polyoxyethylene stearate; sodium oleate; potassium oleate; cetyl ethyl morpholinium ethosulfate; sodium lauryl sulfate; sodium caprylate; sodium caprate; sodium laurate; sodium myristate; sodium cholate; sodium desoxycholate; sodium dihydrocholate; tetradecyltrimethyl ammonium bromide; hexadecylpyridinium chloride; Tween 20; Tween 30; Tween 80, and the like. The amount of surfactant used for producing a pharmaceutically acceptable carrier comprising the beneficial agent, the buffer, and the pharmaceutically acceptable, viscosity-modulating vehicle is about 0.001% to 7.5% by weight. Generally, the compartment 20 composition comprises from 0.5% to 50% beneficial agent, from 20% to 45% aqueous buffer, from 10% to 75% pharmaceutically acceptable, viscosity-modulating vehicle, and from 0.001% to 7.5% surfactant, with the total of all components 100%; and in a more preferred embodiment the composition comprises 25% to 35% beneficial agent, 25% to 35% aqueous buffer solution, 25% to 50% pharmaceutically acceptable, viscosity-modulating vehicle, and 0.01% to 1% surfactant, with the total of all components being 100% by weight. The pharmaceutically acceptable, viscosity-modulating vehicles and the surfactants are known in Pharmaceutical Science, by Remington, 14 Ed., (1970), published by Mack Publishing Co., Easton, Pa., and the buffers are known in Lange's Handbook of Chemists, 13th Ed., (1985), published by McGraw-Hill Co., New York, N.Y, the disclosure of each text being incorporated herein in its entirety by reference.

b. Self-Destructing Shell

According to the principles of the invention, the self-sestructing shell may be a composite 30 (also referred to as a semi-permeable membrane) comprising a biocompatible matrix 31 and a disintegrant 32 dispersed with the matrix 31. The semi-permeable membrane is intended to be rigid enough so as to maintain the physical integrity of the tablet of the invention even in its environment of use without adversely affecting the active agent and to break apart upon the swelling of the embedded disintegrant.

The term "semi-permeable," as defined herein, refers to a membrane which, under identical conditions, transports different molecular species at different rates. In this case, the membrane is permeable to gastrointestinal fluids, yet may or may not be permeable to the active agent or osmotic agent. If it is impermeable to the solubilized or suspended active agent or osmotic agent, it is necessary to include at least one release passageway (also known as a release orifice) through the membrane, while if it is permeable to the active agent or osmotic agent, the release passageway is optional.

In accordance with the practice of this invention, it has now been found that delivery system 10 can be manufactured with a wall section 12 that surrounds the compartment's internal space initially occupied by the beneficial agent formulation. Wall section 12 comprises a composition that does not adversely affect the beneficial agent, the osmopolymer, the osmagent, other ingredients in delivery system 10, the host, or the like.

Wall section 12 preferably comprises a composition comprising means that aids in controlling fluid flux into the compartment area occupied by the expandable driving member (also referred to as a push means). The composition is permeable to the passage of external fluids such as water and biological fluids, and it is substantially impermeable to the passage of beneficial agents, osmopolymers, osmagents, and the like. Typical compositions comprising semipermeable materials for forming wall 12 are, in one presently preferred embodiment, a member selected from the group consisting of a cellulose ester, a cellulose ether and a cellulose esterether. These cellulosic polymers have a degree of substitution, D.S., on the anhydroglucose unit, from greater than 0 up to 3 inclusive. By, "degree of substitution," or "D.S.," is meant the average number of hydroxyl groups originally present on the anhydroglucose unit comprising the cellulose polymer that are replaced by a substituting group. Representative materials include, but are not limited to, a member selected from the group consisting of cellulose acylate, cellulose diacylate, cellulose triacylate, cellulose acetate, cellulose diacetate, cellulose triacetate, mono-, di-, and tricellulose alkanylates, mono-, di-, and tricellulose aroylates, and the like. Exemplary cellulosic polymers include cellulose acetate having a D.S. up to 1 and an acetyl content up to 21% by molecular weight; cellulose acetate having a D.S. of 1 to 2 and an acetyl content of 21% to 35%; cellulose acetate having a D.S. of 2 to 3 and an acetyl content of 35% to 44.8%, and the like. More specific cellulosic polymers include cellulose propionate having a D.S. of 1.8 and a propionyl content of 39.2% to 45% and a hydroxyl content of 2.8% to 5.4%; cellulose acetate butyrate having a D.S. of 1.8 and an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose acetate butyrate having a D.S. of 1.8, and acetyl content of 4% average weight percent and a butyryl content of 51%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentate; coesters of cellulose such as cellulose acetate butyrate and cellulose, cellulose acetate propionate, and the like. The amount of semipermeable materials presently preferred in the shell is about 20% to 100%.

Representative materials that can be used to regulate further the fluid flux of wall 12 include materials that decrease the fluid flux and materials that increase the fluid flux of wall 12. Materials optionally added to the shell for decreasing the flux comprise a member selected from the group consisting of polyacrylate; polymethacrylate; polysulfone; polyacrylic ester; polyacrylonitrile; polyacrylamide; polystyrene; polycaprolactam; polyhexamethylene adipamide; polyhexamethylene sebacamide; polyepoxide; polyformaldehyde, and the like. Materials that increase the permeability of wall section 12 to the passage of an exterior fluid include polyvinyl alcohol; poly(1,4-anhydro-beta-Dmannuroni acid); polyester derived from the condensation of a polyhydric alcohol and a polyfunctional acid wherein the functionality refers to reactive groups such as hydroxyl, carboxyl, and the like; polysaccharides; hydroxy alkylcellulose having a molecular weight of 9,000 to 35,000; polyalkylene glycol, and the like. The concentration of means for regulating the flux in wall 12 is about 5% to 50%.

Wall section 12 optionally comprises a non-toxic plasticizer. Plasticizers operable for the present purpose include straight chain and branched chain plasticizers, cyclic plasticizers, acrylic plasticizers and heterolcyclic plasticizers. Representative plasticizers include a member selected from the group consistent of phthalate, phosphate, citrate, adipate, tartrate, sebacate, succinate, glycolate, glycerolate, benzoate, myristate, sulfonamide and halogenated plasticizer. Generally wall 12 will comprise from 0% to 45% by weight plasticizers or more, with the total concentration of all ingredients in a wall equal to 100%.

Representative plasticizers include dialkyl phthalate, dicycloalkyl phthalate, diaryl phthalate, dimethyl phthalate, dipropyl phthalate, di(2-ethylhexyl)phthalate, di-isopropyl phthalate, alkyl phosphate, aryl phosphate, tributyl phosphate, trioctyl phosphate, tricresyl phosphate and triphenyl phosphate; alkyl citrate, citrate esters, tributyl citrate, triethyl citrate and acetyl triethyl citrate; alkyl adipates such as dioctyl adipate, diethyl adipate and di(2-methoxyethyl)-adipate; dialkyl tartrates such as diethyl tartrate, and butyl tartrate; alkyl sebacates such as diethyl sebacate, dipropyl sebacate and dinonyl sebacate; alkyl succinates such as diethyl succinate and dimethyl succinate; alkylglycolates, alkyl glycerolates, glycol esters and glycerol esters such as glycerol diacetate, glycerol triacetate, glycerol monolactate diacetate, methyl phythayl ethyl glycolate, and the like.

i. Matrix

The matrix comprises a material which can form films or coatings and typically comprises any of the porous membrane materials known in the tabletting art. Typical materials for forming the membranes are those known in the art to form osmosis or reverse osmosis membranes, including polycation-polyanion membranes. The porous membrane materials include, but are not limited to, cellulose acetate, ethylcellulose, polymethacrylic acid esters and acrylic acid ester/methacrylic acid copolymer with quarternary ammonium groups, cellulose triacetate, agar acetate, amylose triacetate, beta glucan acetate, beta glucan triacetate, cellulose acetate ethyl carbamate, cellulose acetate phthalate, cellulose acetate methyl carbamate, cellulose acetate succinate, cellulose acetate dimethylaminoacetate, cellulose acetate ethyl carbonate, cellulose acetate methyl sulfonate, cellulose acetate butyl sulfonate, cellulose ethers, cellulose acetate propionate, polyvinyl methyl ether polymers, cellulose acetate laurate, methyl cellulose, cellulose acetate p-toluene sulfonate, triacetate of locust bean gum, cellulose acetate with acetylated hydroxyethyl cellulose, hydroxylated ethylenevinylacetate, polymeric epoxides, alkylene oxide-alkyl glycidyl ethers, polyurethanes, and polyglycolic acid. Preferably, the membrane material is cellulose acetate, ethylcellulose, polymethacrylic acid esters and acrylic acid ester/methacrylic acid copolymer with quarternary ammonium groups.

Alternatively, the matrix of the self-destructing shell/membrane may be comprised of non-porous membrane materials in which pores have been formed. Typically, this is accomplished by including a water soluble pore-forming material in the insoluble, non-porous membrane material solution. When the membrane is exposed to an aqueous environment, the pore-forming material dissolves, resulting in the formation of pores. Thus, the porosity of the membrane is directly proportional to the amount of pore-forming material incorporated into the membrane. The non-porous membrane materials include, but are not limited to, acrylics, polyurethanes, silicones, polyethylenes, polyvinyl chlorides, and ethylcellulose. The pore-forming materials include, but are not limited to, lactose, sucrose, mannitol, polyethylene glycol (PEG), hydroxypropylmethylcellulose (HPMC) and surfactants or other soluble additives.

ii. Disintegrant

As shown in FIGS. 3–5, the disintegrant is typically a coated sphere 32. It is important that the disintegrant 32 include significant amounts of insoluble, swellable material in a core 34 which cannot be easily expressed (i.e., expelled) through the membrane 30. This aids in causing excessive hydrostatic pressure within the matrix 31 and the rupturing of the semi-permeable membrane, thus allowing massive drug release to occur. For example, insoluble polysaccharides like starch and cellulose which have high water swelling capabilities are preferred, but soluble hydrogels, such as polyethylene glycol, hydroxypropyl methylcellulose and hydroxyethyl cellulose, can be used.

A disintegrant delay jacket 33 is added to impede the flow of external fluid 25 into the system 10. It generally comprises soluble materials, but may contain insoluble materials as well. The delay jacket 33 must be capable of attracting water across the semi-permeable membrane while at the same time hindering the water from reaching the swellable materials core 34 for the designated period of delay. Thus, the delay jacket will typically contain both water soluble, osmotically active components and insoluble and/or swellable components. After the disintegrant delay jacket 33 erodes, external fluid 25 is able to reach the swellable materials core 34. The swellable materials core 34 swiftly swells causing excessive pressure within the rigid or semi-rigid matrix 31 and the rupturing of the semi-permeable membrane 30, thus allowing a burst of drug release to occur.

The delay jacket typically comprises a binder, an osmotic agent, and a tablet lubricant. Suitable binders include, but are not limited to, acacia, alginic acid, carboxymethylcellulose sodium, dextrin, ethylcellulose, gelatin, glucose, guar gum, hydroxyethyl cellulose, hydroxypropyl methylcellulose, hydroxypropyl magnesium aluminum silicate, methylcellulose, microcrystalline cellulose, polyethylene oxide, polymethyl methacrylates, polyvinylpyrrolidone, pregelatinized starch, sodium alginate, syrup, and zein. Suitable osmotic agents include, but are not limited to, inorganic salts such as sodium, potassium or magnesium chloride, or sodium or potassium hydrogen or dihydrogen phosphate; salts of organic acids such as sodium alginate, sodium ascorbate, sodium benzoate, sodium citrate, edetate disodium, sodium fumarate, sodium or potassium acetate, or magnesium succinate; organic acids such as alginic acid, ascorbic acid, citric acid, edetic acid, malic acid, or sorbic acid; carbohydrates such as dextrates, sorbitol, xylitol, maltitol, mannitol, arabinose, ribose, xylose, glucose, dextrose, fructose, galactose, mannose, sucrose, maltose, lactose, or raffinose; water-soluble amino acids such as glycine, leucine, alanine or methionine; or miscellaneous others such as magnesium sulfate, magnesium carbonate, urea, saccharin, sodium saccharin, glycerin, hexylene glycol, polyethylene glycol, or propylene glycol; and mixtures thereof. Suitable tablet lubricants include, but are not limited to, calcium stearate, glyceryl behenate, hydrogenated vegetable oils, magnesium stearate, mineral oil, polyethylene glycol, sodium stearyl fumarate, stearic acid, talc, and zinc stearate.

Additional jacket excipients may include glidants and wetting agents. Suitable glidants include, but are not limited to, fused or colloidal silicon dioxide, calcium silicate, magnesium silicate, talc, and silica hydrogel. Suitable wetting agents include, but are not limited to, benzalkonium chloride, benzethonium chloride, cetylpyridinium chloride, docusate sodium, lecithin, nonoxynol 9, nonoxynol 10, octoxynol 9, poloxamer, polyoxyl 35 castor oil, polyoxyl 40 hydrogenated castor oil, polyoxyl 50 stearate, polyoxyl 10 oleyl ether, polyoxyl 20 cetostearyl ether, polyoxyl 40 stearate, polysorbate 20, polysorbate 40, polysorbate 60, 80, sodium lauryl sulfate, sorbitan esters, polyoxyethylene sorbitan fatty acid esters, and Tyloxapol (4-(1,1,3,3-tetramethylbutyl)phenol polymer with formaldehyde and oxirane).

Certain excipients may be included within the device to serve more than one function. For example, glucose may be included as a binder and/or an osmotic agent, and talc may be included as a glidant and/or a lubricant.

As shown in FIG. 6, in an alternate embodiment, of wall 12 may comprise a laminate 38 made up of a swelling agent core lamina 35 in contact with an inner delay jacket lamina 37 and outer delay jacket lamina 36. The inner and outer delay jacket lamina are then in contact with a matrix lamina 30. When external fluid 25 reaches the inner and/or outer delay jackets, the jacket erodes over time to allow the device to travel through the digestive tract and reach the colon. When external fluid 25 reaches the swelling agent core lamina 35, the swellable materials core lamina 35 swiftly swells causing excessive pressure within the rigid or semi-permeable membrane lamina 30 and the rupturing of the semi-permeable membrane 30, thus allowing a burst of drug release to occur.

The semi-permeable membrane containing the disintegrant embedded in the matrix may be applied using conventional coating techniques known in the art, for example fluidized bed spraying and compression coating. The choice of semi-permeable membrane plays an important role in controlling the release of the active agent. For example, it is known that the acetyl value is an important factor in determining the release rate from membranes constructed from cellulose acetate. Compendial grade cellulose acetate is commercially available with nominal acetyl values of either 32% or 40% by weight. Membranes constructed from material at 32% by weight acetyl value release drug from similar drug cores at a faster rate than do membranes constructed with the same amount of cellulose acetate by weight having a 40% acetyl value.

c. Delay Jacket

A delay jacket may be added to impede the dissolution and release of the active agent for the time necessary for the drug delivery device to travel through the small intestine. It generally comprises soluble materials, but may contain insoluble materials as well. The delay jacket must be capable of attracting water across the semi-permeable membrane while at the same time hindering the water from reaching the active core for the designated period of delay. Thus, the delay jacket will typically contain both water soluble, osmotically active components and insoluble and/or swellable components. The soluble osmotic agents leach out of the jacket and a suspension of at least some of the insoluble and/or swellable components remains. The active agent will later diffuse through this remaining suspension and thus the release of the active agent is dependent not only upon the composition of the inner core, but also upon the composition of the jacket.

The delay jacket typically comprises a binder, an osmotic agent, and a tablet lubricant. Suitable binders include, but are not limited to, acacia, alginic acid, carboxymethylcellulose sodium, dextrin, ethylcellulose, gelatin, glucose, guar gum, hydroxyethyl cellulose, hydroxypropyl methylcellulose, hydroxypropyl magnesium aluminum silicate, methylcellulose, microcrystalline cellulose, polyethylene oxide, polymethylmethacrylates, polyvinylpyrrolidone, pregelatinized starch, sodium alginate, syrup, and zein. Suitable osmotic agents include, but are not limited to, inorganic salts such as sodium, potassium or magnesium chloride, or sodium or potassium hydrogen or dihydrogen phosphate; salts of organic acids such as sodium alginate, sodium ascorbate, sodium benzoate, sodium citrate, edetate disodium, sodium fumarate, sodium or potassium acetate, or magnesium succinate; organic acids such as alginic acid, ascorbic acid, citric acid, edetic acid, malic acid, or sorbic acid; carbohydrates such as dextrates, sorbitol, xylitol, maltitol, mannitol, arabinose, ribose, xylose, glucose, dextrose, fructose, galactose, mannose, sucrose, maltose, lactose, or raffinose; water-soluble amino acids such as glycine, leucine, alaninc or methionine; or miscellaneous others such as magnesium sulfate, magnesium carbonate, urea, saccharin, sodium saccharin, glycerin, hexylene glycol, polyethylene glycol, or propylene glycol; and mixtures thereof. Suitable tablet lubricants include, but are not limited to, calcium stearate, glyceryl behenate, hydrogenated vegetable oils, magnesium stearate, mineral oil, polyethylene glycol, sodium stearyl fumarate, stearic acid, talc, and zinc stearate.

Additional jacket excipients may include glidants and wetting agents. Suitable glidants include, but are not limited to, fused or colloidal silicon dioxide, calcium silicate, magnesium silicate, talc, and silica hydrogel. Suitable wetting agents include, but are not limited to, benzalkonium chloride, benzethonium chloride, cetylpyridinium chloride, docusate sodium, lecithin, nonoxynol 9, nonoxynol 10, octoxynol 9, poloxamer, polyoxyl 35 castor oil, polyoxyl 40 hydrogenated castor oil, polyoxyl 50 stearate, polyoxyl 10 oleyl ether, polyoxyl 20 cetostearyl ether, polyoxyl 40 stearate, polysorbate 20, polysorbate 40, polysorbate 60, 80, sodium lauryl sulfate, sorbitan esters, polyoxyethylene sorbitan fatty acid esters, and Tyloxapol (4-(1,1,3,3-tetramethylbutyl)phenol polymer with formaldehyde and oxirane).

Certain excipients may be included within the device to serve more than one function. For example, glucose may be included as a binder and/or an osmotic agent, and talc may be included as a glidant and/or a lubricant.

The composition of the delay jacket should be tailored to the composition, type of core, and type of membrane used. The delay jacket may be applied to the core using conventional means known in the technology, for example by using a tablet press or a spray coater. If applied as a solid, the delay jacket is preferably between about 125% and about 275%, and more preferably between about 150% and about 250% of the core by weight. If applied as a liquid, the delay jacket is preferably between about 10% and about 100%, more preferably between about 20% and about 80%, and most preferably between about 30% and about 60% of the core by weight. However, in both cases the ranges will vary considerably based on the solution/suspension properties of the materials selected, and on the permeability properties of the rate controlling membrane.

Such device with an enteric coating thus resists dissolution in gastric fluid for at least two hours and thereafter limits the release of active agent in intestinal fluid to approximately ten percent or less for at least three hours after the device passes through the pylorus due to the delay jacket. The device thus allows for controlled continuous release of the active agent in the pre-selected region of the gastrointestinal tract at a predetermined average rate, preferably at a rate of about 5 percent to about 25 percent by weight per hour. In addition, the device allows for substantially all of the active agent to be released at the pre-selected region of the gastrointestinal tract, preferably 70–100% within twenty-four hours of ingestion.

d. Expandable, Volume Consuming, Push Means (Piston Pump)

The expandable push means 50 operable for pushing the beneficial agent composition 23 from delivery system 10, comprises, in a presently preferred embodiment, a swellable hydrophilic polymer. Hydrophilic polymers are known also as osmopolymers. The push means 50 interacts with water and aqueous biological fluids and swells or expands. Osmopolymers exhibit the ability to swell in water and to retain a significant portion of the imbibed and absorbed water within the polymer structure. The osmopolymers swell or expand to a very high degree, usually exhibiting a 2 to 50 fold volume increase. The osmopolymers can be noncross-linked or cross-linked. The swellable, hydrophilic polymers are, in one presently preferred embodiment, lightly cross-linked, such as cross-links being formed by covalent or ionic bonds. The osmopolymers can be of plant, animal or synthetic origin. Hydrophilic polymers suitable for the present purpose include poly(hydroxyalkylmethacrylate) having a molecular weight of from 30,000 to 5,000,000; poly(vinylpyrrolidone) having molecular weight of from 10,000 to 360,000; anionic and cationic hydrogels; polyelectrolyte complexes; poly(vinyl alcohol) having a low acetate residual, cross-linked with glyoxal, formaldehyde, or glutaraldehyde and having a degree of polymerization from 200 to 30,000; a mixture of methyl cellulose, cross-linked agar and carboxymethyl cellulose; a water insoluble, water swellable copolymer produced by forming a dispersion of finely divided copolymer of maleic anhydride with styrene, ethylene, propylene, butylene or isobutylene cross-linked with from 0.0001 to about 0.5 moles of polyunsaturated cross-linking agent per mole of maleic anhydride in the copolymer; water swellable polymers of N-vinyl lactams, and the like.

Other osmopolymers operable as the expandable driving member 50 (also referred to as the push means) and initially surrounded by wall section 12 comprise polymers that form hydrogels such as Carbopol® acidic carboxy polymers generally having a molecular weight of 450,000 to 4,000,000; the sodium salt of Carbopol® acidic carboxy polymers and other metal salts; Cyanamer® polyacrylamides; cross-linked water swellable indine-maleic anhydride polymers;

Goodrite® polyacrylic acid having, but not limited to, a molecular weight of 80,000 to 200,000, and the sodium and other metal salts; Polyox® polyethylene oxide polymers having a molecular weight of 100,000 to 5,000,000; starch graft copolymers; AquaKeeps® acrylate polymers; diester cross-linked linked polyglucan, and the like. Representative polymers that form hydrogels are known to the prior art in U.S. Pat. No. 3,865,108 issued to Hartop; U.S. Pat. No. 4,002,173 issued to Manning; U.S. Pat. No. 4,207,893 issued to Michaels, and in Handbook of Common Polymers, by Scott and Roff, published by the Chemical Rubber Company, CRC Press, Cleveland, Ohio, the disclosure of each of these publications being incorporated herein in its entirety by reference.

In general the amount of water present in a hydrogel is at least 20 weight percent of the total weight of the dry polymer. The most characteristic property of these hydrogels is that it swells in the presence of water and shrinks in the absence of water. The extent of swelling (equilibrium water content) is determined by the nature (mainly the hydrophilicity) of the polymer chains and the crosslinking density.

The kinetics of hydrogel swelling is limited by the diffusion of water through the outer layers of the dried hydrogel. Therefore, while hydrogels swell to a large extent in water, the time it takes to reach equilibrium swelling may be significant, depending on the size and shape of the hydrogel. To reduce the amount of time it takes for a hydrogel to reach equilibrium, hydrogel foams may be used. Hydrogels foams may be made by crosslinking polymers in the presence of gas bubbles. The hydrogels foams prepared with macroscopic gas cells will have an open celled structure similar to sponges except that the pore size will generally be an order of magnitude larger.

The expandable push means 50 in another preferred embodiment comprises an optional osmagent 26 dispersed therein. The osmagents are known also as osmotically effective solutes and they are also known as osmotically effective compounds. The osmotically effective compounds that can be used for the purpose of this invention include inorganic and organic compounds that exhibit an osmotic pressure gradient across a semipermeable wall. The osmotically effective compounds, along with the osmopolymers, imbibe fluid into the device thereby making available in situ fluid for imbibition by an osmopolymer to enhance its expansion. The osmotically effective compounds are used by mixing them with the osmopolymer, homogeneously or heterogeneously and then charging them into the delivery system. Osmotically effective solutes used for the former purpose include magnesium sulfate, magnesium chloride, sodium chloride, potassium chloride, potassium sulfate, sodium sulfate, lithium sulfate, potassium acid phosphate, d-mannitol, urea, inositol, magnesium succinate, tartaric acid, carbohydrates such as raffinos, sucrose, glucose, alpha-d-lactose monohydrate, mannitol, and mixtures thereof. The amount of osmagent in the blend with the osmopolymer usually is from 1% to 40%, or higher, with the total of all ingredients comprising the second composition equal to 100%.

The expandable push means 50 in another preferred embodiment comprises an osmagent. The osmagent can comprise a tablet, a layer, or osmagent can be pressed into wall section 12. The osmagent can be in any suitable form such as particles, crystals, pellets, granules, and the like, when pressed into a tablet layer and into wall section 12. Various osmotically effective solutes comprising magnesium sulfate, magnesium chloride, sodium chloride, lithium chloride, potassium sulfate, sodium carbonate, sodium sulfite, lithium sulfate, potassium chloride, calcium carbonate, potassium acid phosphate, sodium lactate, calcium lactate, mannitol, urea, inositol, magnesium succinate, tartaric acid, soluble carbohydrates such as raffinose, sucrose, glucose, lactose, mixtures thereof, and the like, can be used for this embodiment. The osmotic pressure of an osmagent, or an osmopolymer, can be measured using an osmometer. An osmometer used for the present measurements is identified as Model 320B, Vapor Pressure Osmometer, manufactured by the Hewlett Packard Co., Avondale, Pa. Osmagents and osmopolymers are known to the art in U.S. Pat. Nos. 4,327,725 and 4,612,008, the disclosure of each of these patents being incorporated herein in its entirety by reference.

Other gelable, fluid imbibing and retaining polymers useful for forming the hydrophilic, expandable push means 50 include pectin having a molecular weight ranging from 30,000 to 300,000; polysaccharides such as agar, acacia, karaya, traga anth, algins and guar; Carbopol® acidic carboxy polymer and its salt derivatives; polyacrylamides; water-swellable indene maleic anhydride polymers; Goodrite® polyacrylic acid having a molecular weight of 80,000 to 200,000; Polyox® polyethylene oxide polymers having a molecular weight of 100,000 to 7,500,000; starch graft copolymers; Aqua-Keep® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000; and the like. In a preferred embodiment, the expandable member is formed from polymers and polymeric compositions that are thermoformable. Representative polymers possessing hydrophilic properties are known in U.S. Pat Nos. 3,865,108; 4,002,173; 4,207,893; 4,327,725, and in Handbook of Common Polymers; by Roff and Scott, published by Cleveland Rubber Company, Cleveland, Ohio, the disclosure of each of these documents being incorporated herein in its entirety by reference.

e. Osmotic Agent

The core may include an osmotic agent if necessary or desirable to effect the desired release profile. The active agent may be sufficiently soluble to induce an internal hydrostatic pressure acceptable to eliminate the need for any additional osmotic agent. Generally, however, an additional agent will be included as the osmotic agent so as to promote the dissolution and release of the core active agent. The osmotic agent is a water-soluble compound which induces a hydrostatic pressure after water passes the semi-permeable membrane to drive out the active agent as a solution or a suspension. Suitable osmotic agents include any number of agents having a suitably high solubility and dissolution rate. The osmotic agent may be selected from any pharmaceutically acceptable chemical entity which is inert to the system. Suitable osmotic agents include pharmaceutically acceptable salts of inorganic and organic acids or nonionic organic acids of particularly high water solubility, e.g., carbohydrates such as sugar, or amino acids, or another active agent possessing suitable solubility.

Examples of such water-soluble compounds for inducing osmosis in the core include inorganic salts such as sodium, potassium or magnesium chloride, or sodium or potassium hydrogen or dihydrogen phosphate; salts of organic acids such as sodium alginate, sodium ascorbate, sodium benzoate, sodium citrate, edetate disodium, sodium fumarate, sodium or potassium acetate, or magnesium succinate; organic acids such as alginic acid, ascorbic acid, citric acid, edetic acid, malic acid, or sorbic acid; carbohydrates such as dextrates, sorbitol, xylitol, maltitol, mannitol, arabinose, ribose, xylose, glucose, dextrose, fructose, galactose, mannose, sucrose, maltose, lactose, or raffinose; water-soluble amino acids such as glycine, leucine, alanine or methionine; or miscellaneous others such as magnesium sulfate, magnesium carbonate, urea, saccharin, sodium saccharin, glycerin, hexylene glycol, polyethylene glycol, or propylene glycol; and mixtures thereof.

f. Additional Core Excipients

Additional core excipients may include tabletting lubricants, glidants, wetting agents to aid in dissolution of the components, binders, and suspending/thickening agents. Suitable lubricants include, but are not limited to, calcium stearate, glyceryl behenate, hydrogenated vegetable oils, magnesium stearate, mineral oil, polyethylene glycol, sodium stearyl fumarate, stearic acid, talc, and zinc stearate. Suitable glidants include, but are not limited to, fused or colloidal silicon dioxide, calcium silicate, magnesium silicate, talc, and silica hydrogel. Suitable wetting agents include, but are not limited to, benzalkonium chloride, benzethonium chloride, cetylpyridinium chloride, docusate sodium, lecithin, nonoxynol 9, nonoxynol 10, octoxynol 9, poloxamer, polyoxyl 35 castor oil, polyoxyl 40 hydrogenated castor oil, polyoxyl 50 stearate, polyoxyl 10 oleyl ether, polyoxyl 20 cetostearyl ether, polyoxyl 40 stearate, polysorbate 20, polysorbate 40, polysorbate 60, polysorbate 80, sodium lauryl surfate, sorbitan esters, polyoxyethylene sorbitan fatty acid esters, and Tyloxapol (4-(1,1,3,3-tetramethylbutyl)phenol polymer with formaldehyde and oxirane). Suitable binders include, but are not limited to, acacia, alginic acid, carboxymethylcellulose sodium, dextrin, ethylcellulose, gelatin, glucose, guar gum, hydroxyethyl cellulose, hydroxypropyl methylcellulose, hydroxypropyl magnesium aluminum silicate, methylcellulose, microcrystalline cellulose, polyethylene oxide, polymethylmethacylates, polyvinylpyrrolidone, pregelatinized starch, sodium alginate, syrup, and zein. Suitable suspending/thickening agents include acacia, agar, alginic acid, bentonite, carbomer, carboxymethylcellulose calcium, carageenan, carboxymethylcellulose sodium, corn starch, dextrin, gelatin, guar gum, hydroxyethyl cellulose, hydroxypropyl cellulose, hydroxypropyl methylcellulose, kaolin, lecithin, magnesium aluminum silicate, methylcellulose, microcrystalline cellulose, pectin, poloxamer, polyethylene glycol alginate, polyethylene oxide, polyvinyl alcohol, polyvinylpyrrolidone, vinyl acetate, powdered cellulose, pregelatinized starch, propylene glycol alginate, silicon dioxide, sodium alginate, tragacanth, and xanthan gum.

g. Exit Means

The delivery device 10 preferably comprises an exit means in the shell or housing means for connecting the exterior with the interior of the delivery system for delivering the agent formulation from the delivery system.

The phrase, "exit means," as used herein, comprises means and methods suitable for the metered release of the beneficial agent 23 from compartment 20 of delivery system 10. The exit means includes at least one passageway 60, orifice, or the like, through wall 12 for communicating with compartment 20. The expression, "at least one passageway," includes aperture, orifice, bore, pore, porous element through which the agent can migrate, hollow fiber, capillary tube, porous overlay, porous insert, and the like. The expression also includes material that erodes or is leached from the wall in the fluid environment of use to produce at least one passageway in dosage form 10. Representative material suitable for forming at least one passageway, or a multiplicity of passageways, include an erodible poly(glycolic) acid or poly(lactic) acid member in the wall; a gelatinous filament; poly(vinyl alcohol); leachable materials such as fluid removable pore forming polysaccharides, salts, or oxides, and the like. The expression includes structural characteristics that concentrate stress at a precise point in the wall so that only a small amount of force will induce breakage in the wall, yielding a passageway through the wall from compartment 20 to the outside of the device. A passageway or a plurality of passageways can be formed by leaching a material such as sorbitol, lactose and like water-soluble solids from the wall. The passageway can have any shape such as round, triangular, square, elliptical, and the like, for assisting in the metered release of beneficial agent from dosage form 10. Dosage form 10 can be constructed with one or more passageways in spaced apart relations or more than a single surface of a dosage form. Passageways and equipment for forming passageways are disclosed in U.S. Pat. Nos. 3,845,770; 3,916,899; and 4,008,864, the disclosure of each of these documents being incorporated herein in its entirety by reference.

In general, one or more release orifices may be included through the self-destructing shell. This release orifice is included to allow passage of the active agent and the soluble excipients, either in addition to or as an alternative to the pores of the semi-permeable membrane. It can be used to further control the release rate of the active agent by varying its size. Typically, the size of the release orifice is between about 0.05 mm and about 1.5 mm, more narrowly between about 0.15 mm and about 0.40 mm for elementary OROS, however, this range is considerably higher for more complicated systems such as MOCOS which utilize viscous hydrogel polymers. The release orifice may be added using conventional techniques known in the art, for example by drilling, either mechanically or by use of a laser. Further, at least one preferential weak spot may be created within the coating such that the pressure which builds up within the device causes a breakthrough in the coating at such weakened areas.

h. Diaphragm or Partition Layer

Compartment 20 optionally comprises a diaphragm 70 positioned between the beneficial agent formulation and the expandable push means 50. Diaphragm 70, in a presently preferred embodiment, comprises a composition that is substantially impermeable to the passage of fluid and it serves to restrict the passage of fluid present in the expandable driving member (i.e., push means) into the beneficial agent formulation; and it operates to essentially maintain the integrity of the beneficial agent formulation and the driving diaphragm. Diaphragm 70 acts also to insure that the expanding driving force generated by the expandable driving member is applied directly against the beneficial agent formulation. In operation, as the expandable push means 50 absorbs and imbibes fluid, it expands and pushes against diaphragm 70 causing it to slide inside compartment 20. Diaphragm 70 moves towards passageway 60, pushing the beneficial agent formulation through passageway 60 for maximizing the delivery of the beneficial agent to a biological environment of use.

Diaphragm 70, positioned between the beneficial agent composition and the expandable driving member, is a means for (1) maintaining the separate identity of the beneficial agent composition and the driving member, for (2) transmitting the force generated by the driving member against the beneficial agent composition, and (3) for substantially restricting the passage of fluid between the beneficial agent composition and the driving member. Diaphragm 70 comprises in one embodiment, an olefin, a vinyl, a condensation, an addition, an organosilicon, or an inorganic polymer. More specific polymer composition comprise high density polyethylene, high density polypropylene, polystyrene, polycarbonate, polyamide, elastomers, chlorinated rubber, styrene-butadiene rubber, chloroprene rubber, silicone, glass, and the like. In an alternate embodiment, diaphragm 70 comprises a wax. More preferably, the waxes exhibit a melting point or a solidification point of about 45° C. or higher, usually 45° C. to 110° C. The waxes are selected from mineral, vegetable, plant, fish, animal, petroleum, and synthetic waxes. Representative waxes comprise a member selected from the group consisting of montan wax, ozokerite wax, carnuba wax, myricyl cerotate wax, beeswax, spermaceti wax, ceresini wax, gama wax, Japan wax, ouricury wax, ceresin wax, castor wax, Witco wax, polyethylene wax, and the like. Additionally, reinforcing agents such as Cabo-sil® material can be incorporated into the wax for improving its structural integrity. In another manufacture, diaphragm 70 can comprise a polymer elastomer possessing properties of low Shore A hardness, and Young's modulus, thermoplastic or thermoset, and essentially water impermeable.

i. Additional Coatings

An enteric delay jacket coating 40 may be included to prevent the dissolution of the jacket and core in the stomach. It may consist of any pharmaceutically acceptable material which is gastric fluid resistant, that is a material soluble only in fluids with a pH greater than that of the stomach. Enteric coating materials include, but are not limited to, cellulose acetate phthalate NF, hydroxypropyl methylcellulose phthalate NF, polyvinyl acetate phthalate NF, and methacrylic acid copolymer NF. Thus, in a low pH environment, the enteric coating will be insoluble and hinder intrusion of water through the semi-permeable membrane which could otherwise dissolve the delay jacket. It may be applied over the semi-permeable membrane using conventional film coating techniques known in the art, for example perforated pan coating.

Upon ingestion, the drug delivery device encounters the acidic gastric fluid, but remains intact because of the enteric coating. After the stomach pushes the device through the pylorus into the duodenum, the device is exposed to fluids of higher pH and the enteric coating dissolves. Once the semi-permeable membrane is exposed to these fluids, the device is activated. Water from the gastrointestinal tract is imbibed through the membrane by diffusion and begins to selectively dissolve any delay jacket which may be present. The delay jacket directly under the membrane prevents water from reaching the active drug core, thus providing the delayed release of the active agent. Eventually, the delay jacket is eroded and external fluid reaches the active core, increasing the pressure within the membrane as the core swelling agents imbibe more and more water. As the drug is dissolved or suspended, this hydrostatic pressure forces the active agent through the membrane and/or through the release orifice to deliver the drug at a controlled rate. The release rate of the drug is based on the swelling properties of the swelling agent included in the core, the solubility of the drug and excipients, and the water permeation rate through the membrane, and the size of the membrane pores or release orifice.

As an extension to the basic device, a further layer of active agent 80 may be included to deliver an initial burst of active agent when reaching the stomach. This active agent 80 may be the same as or different from that within the core cavity 20. The additional active agent layer 80 may be applied over the semi-permeable membrane 30 or enteric coating 40 to deliver an immediate release of active agent or a loading dose to compensate for the lag time between ingestion of the device and release of the core active agent 23. Alternatively, this additional layer 80 may be applied under the enteric layer for release in the upper portion of the small intestine. This additional agent layer 80 comprises one or more active agent and may optionally include other pharmaceutically acceptable excipients including osmotic agents, lubricants, glidants, wetting agents, binders, fillers, and suspending/thickening agents.

Manufacturing

The delivery system of the present invention is manufactured by standard techniques. For example, in one manufacture the beneficial drug and other ingredients comprising the core are blended and pressed into a solid layer. The drug and other ingredients can be blended also with a solvent and mixed into a solid or semisolid form by conventional methods such as ballmilling, calendering, stirring or rollmilling and then pressed into a preselected shape. Next, a layer of osmopolymer is placed in contact with the layer of drug in a like manner. The layering of the drug formulation and the osmopolymer hydrogel layer can be fabricated by conventional two-layer press techniques. The two contacted layers may be first coated with a drug-free semipermeable wall and then with the optional enteric coat. The drug-free delayed composition can be applied by press coating, molding, spraying, dipping, and air suspension procedures.

In another manufacture, the dosage form is manufactured by the wet granulation technique. In the wet granulation technique the drug and the ingredients comprising the first layer are blended using an organic cosolvent, such as isopropyl alcohol-methylene dichloride 80/20 v/v (volume/volume) as the granulation fluid or anhydrous denatured ethanol. The ingredients forming the active agent layer are individually passed through a 20 mesh screen and then thoroughly blended in a mixer. Next, other ingredients comprising the first layer are dissolved in a portion of the granulation fluid described above. Then, the latter prepared wet blend is slowly added to the drug blend with continual mixing in the blender. The granulating fluid is added until a wet blend is produced, which wet mass blend is then forced through a 20 mesh screen onto oven trays. The blend is dried for 18 to 24 hours at 35° C. in a forced air oven. The dried granules are then sized with a 20 mesh screen. Next, magnesium stearate is added to the dry screened granule blend. The granulation is then put into milling jars and mixed on a jar mill for 5 to 10 minutes. The composition is pressed into a layer, for example in a Manesty® layer press. The speed of the press is set at 30 rpm and the maximum load set at 2 tons. The active agent layer is pressed against the composition forming the expandable driving means displacement layer to form the bilayer tablets. The bilayer tablets are coated with a semipermeable shell.

Another manufacturing process that can be used for providing compartment 20 composition comprises blending the powdered ingredients in a fluid bed granulator. After the powdered ingredients are dry blended in the granulator, a granulating fluid, for example, a granulating polymer in water, is sprayed onto the powders. The polymer coated powders are than dried in the granulator. This process granulates all the ingredients present therein while adding the granulating fluid. After the granules are dried, a lubricant such as stearic acid or magnesium stearate is added to the granulator. The granules are then pressed in the manner described above.

The following examples are presented to further illustrate and explain the present invention and should not be taken as limiting in any regard.

EXAMPLES

Example 1

Determination of Shell Thickness and Pore size Materials and Methods

The formulation and preparation of the drug core tablet, the hydrogel and the compression coat (shell) were optimized based on preliminary studies. In the first part of this study, we studied the effect of the amount of shell and the delivery orifice size on the release of a water soluble marker, methylene blue.

Methylene Blue Core Tablets

The core tablets were prepared as follows: 2.25 g of methylene blue (Fisher Scientific, Fairlawn, N.J.) and 20.25 g of lactose (Pfanstiehl Laboratories, Waukegon, Ill.) were mixed and kneaded with dropwise addition of distilled water (5 mL). The moist dough was passed through a 0.8 mm screen and allowed to dry for 20 hours at room temperature. The dried mixture was again screened through a 0.8 mm screen. Then 2.5 g of PEG 6000 (Matheson, Coleman and Bell Manufacturing Chemists, Norwood, Ohio) was blended into the mixture and the granules compressed into either 7 mm or 9 mm dia. biconvex tablets having a hardness of approximately 1 kp. The tablets (50 mg each) were compressed individually on a Carver Laboratory Press (Model C, Fred S. Carver, Inc., Menomonee Falls, Wis.).

Compression Coat Shell 1.35 mL of 10% Tween 80 (Hilltop Research, Inc., Miamisville, Ohio) and 1.14 mL of 10% glycerin (Fisher Scientific) were mixed. 15 g of Ethocel® 45cps (Dow Chemical Company, Midland, Miss.) was spread on a foil tray and warmed to 60° C. The Tween 80/glycerin mixture was sprayed evenly, using a spray bottle, on the Ethocel®. This was then warmed to 60° C. for 1 to 2 hours and the drying completed overnight at room temperature. Three different shell amounts, 300, 375 and 425 mg were studied.

The final product was prepared as follows. Half of the appropriate amount of the shell granules were placed into the die. The core tablet was then centered over it by hand. Finally, the remaining shell granules were added and the tablets compressed on a Carver Laboratory Press using flat faced punches, 13 mm dia., to an approximate hardness of 9 kp. Additional tablets were also made with the 7 mm core and 375 mg shell and having a hardness of approximately 13.4 kp. The delivery orifices were made manually using the appropriate size drill bits (E & J Swiggart Co., Cincinnati, Ohio).

The in vitro release profiles of methylene blue from the delivery system were studied in 900 mL of distilled water containing 0.02% Tween 80 and maintained at 37° C. The U.S.P. paddle dissolution method (United States Pharmacopeia, XXI Edition, (1985), pp. 1243–1244) was used with the rotation speed of the paddles maintained at 100 rpm. The disclosure of pp. 1243–1244 of the Pharmacopeia is incorporated herein in its entirety by reference. Samples (3 mL) were withdrawn, with replacement, from the dissolution vessels and the methylene blue content was determined spectrophotometrically at 609 nm.

The in vitro release profiles were fitted to four different equations. The Higuchi equation (Hig) describes the % release vs (time)$^{1/2}$ profile. The Hixon-Crowell (H-C) equation relates $W_o^{1/3} - W_t^{1/3}$ to time, where, $W_o$ is the amount remaining to be released at time 0 and $W_t$ is the amount remaining to be released at time t. The Sigma Minus numeric (S-N) relationship is between numeric % remaining to be released and time whereas the Sigma Minus Semilog (S-L) is between log(% remaining to be released) and time.

Results and Discussion

Figure 10:
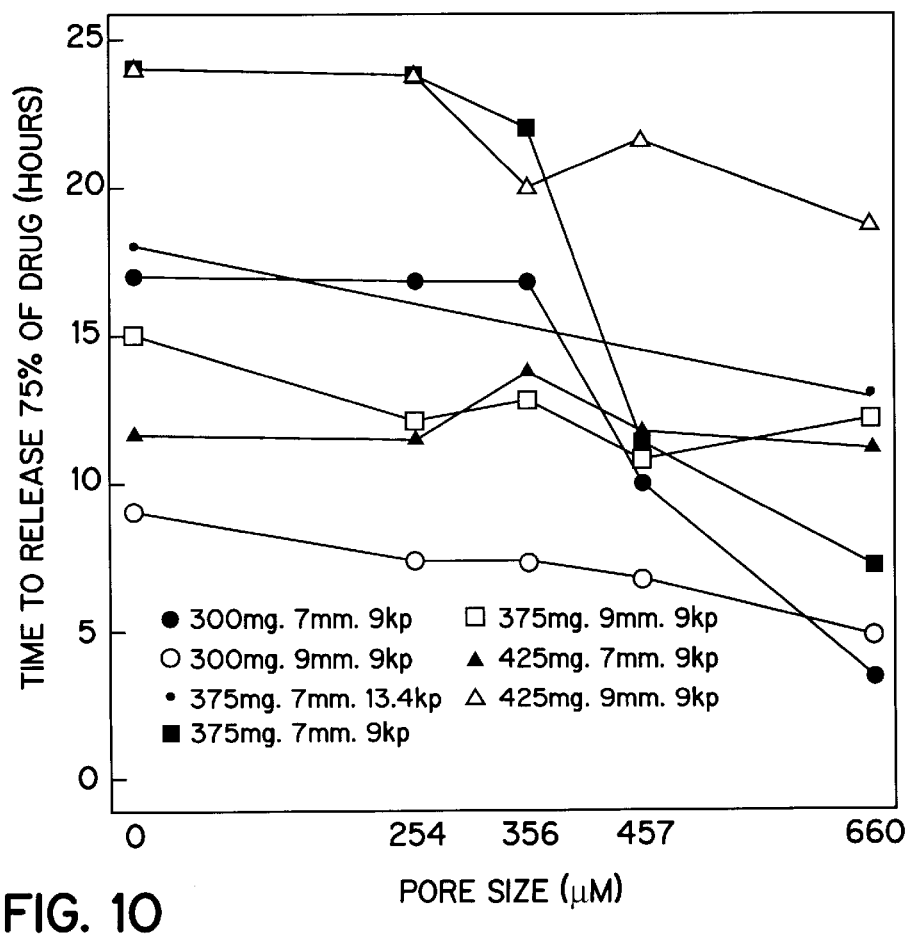
FIG. 10 shows the effect of delivery orifice (pore) size on the time to release 75% of the drug from the system.

The effect of delivery orifice (pore) size on the time to release 75% of the drug from the system is shown in FIG. 10. As seen from the figure, increase in the pore size leads to a reduction in the time to release 75% of the drug.

Figure 11:
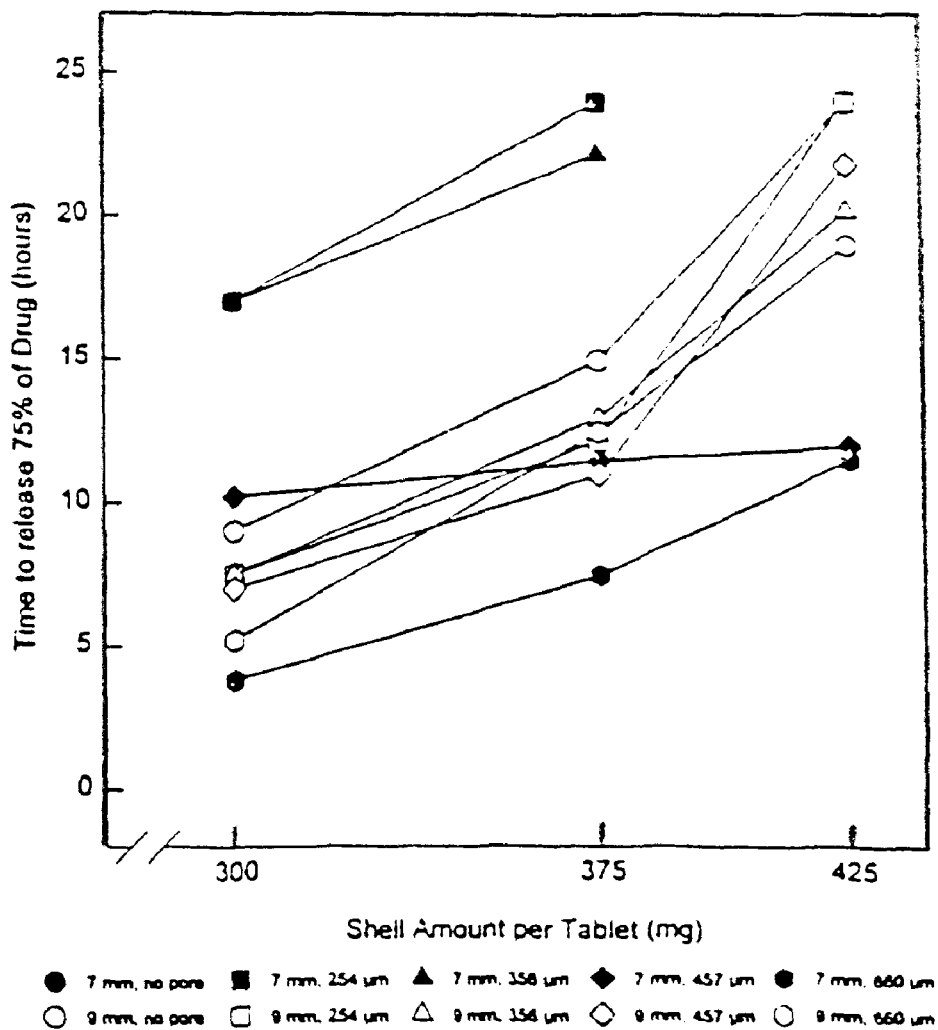
FIG. 11 shows the effect of shell amount on the time to release 75% of drug from the delivery system.
Figure 12A:
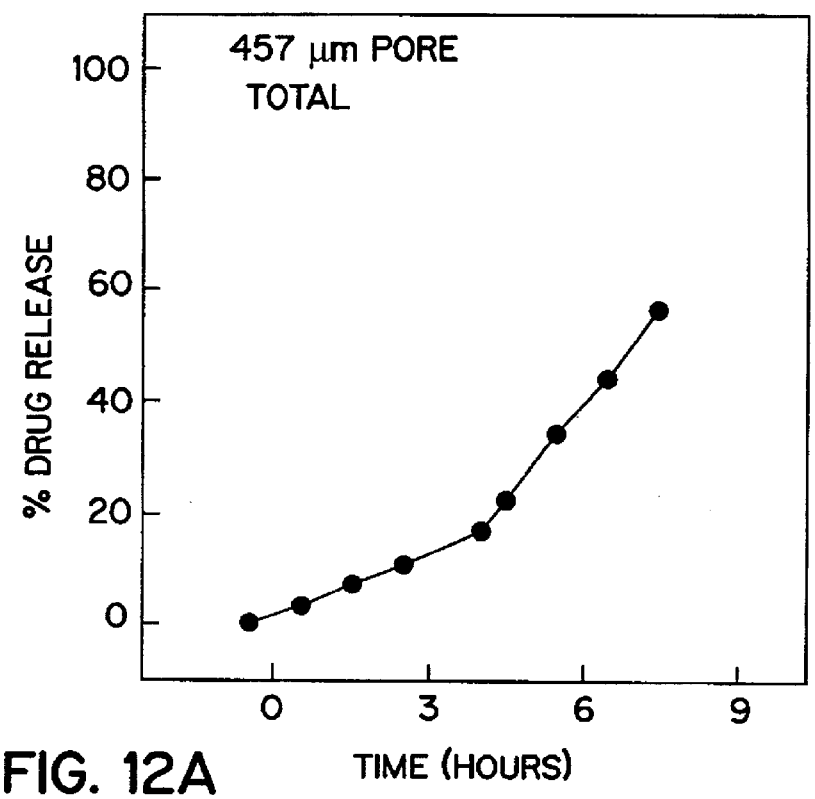
FIG. 12 shows the percent of drug released across the 300 mg shell and through the pore.
Figure 12B:
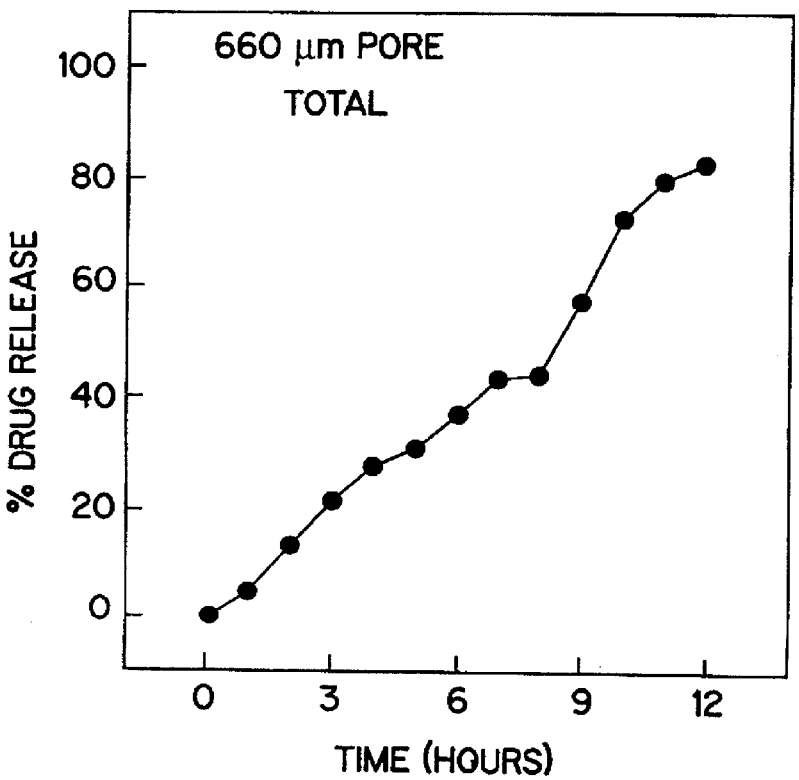
Figure 12C:
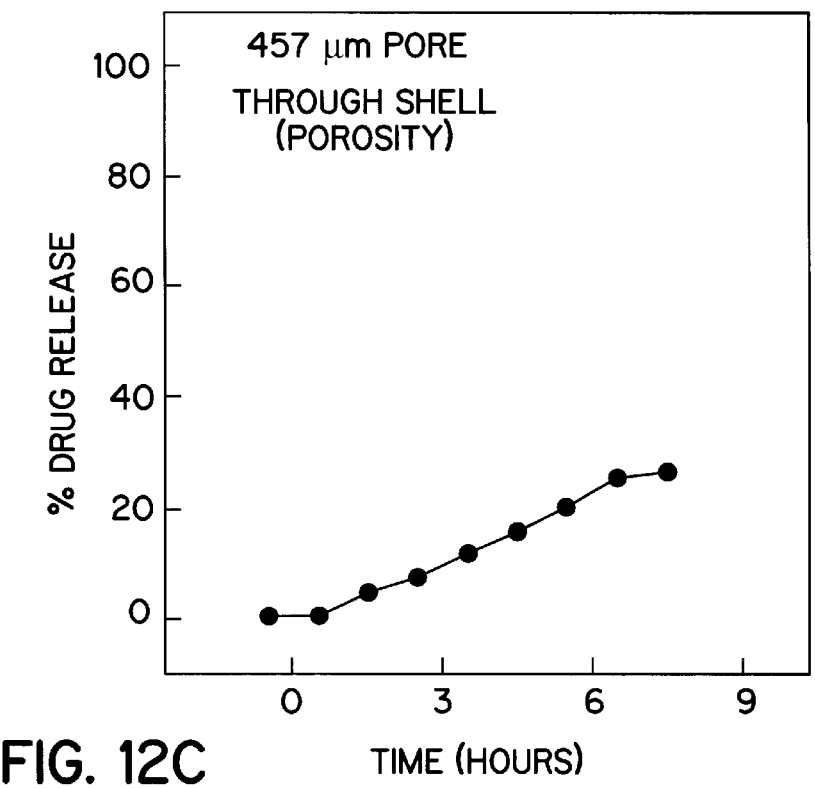
Figure 12D:
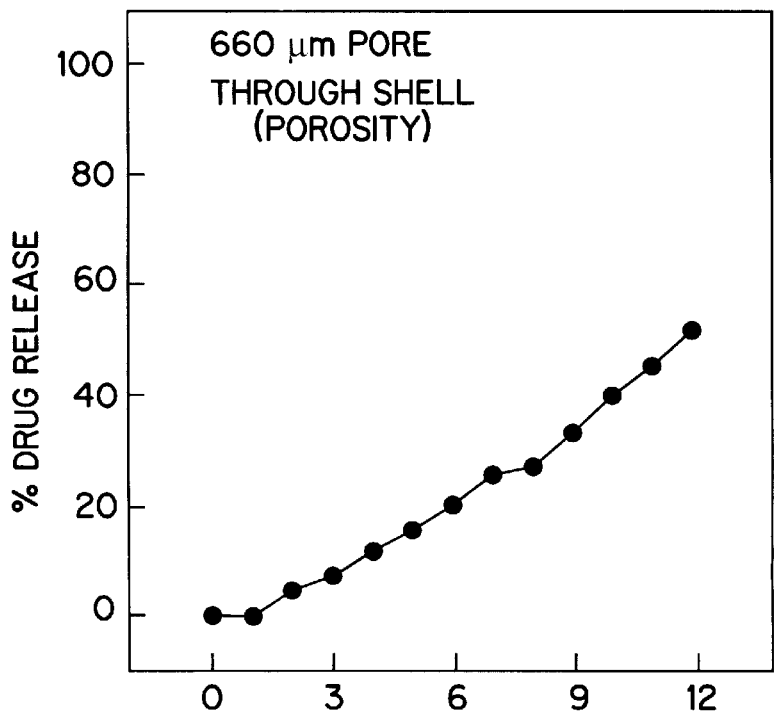
Figure 12E:
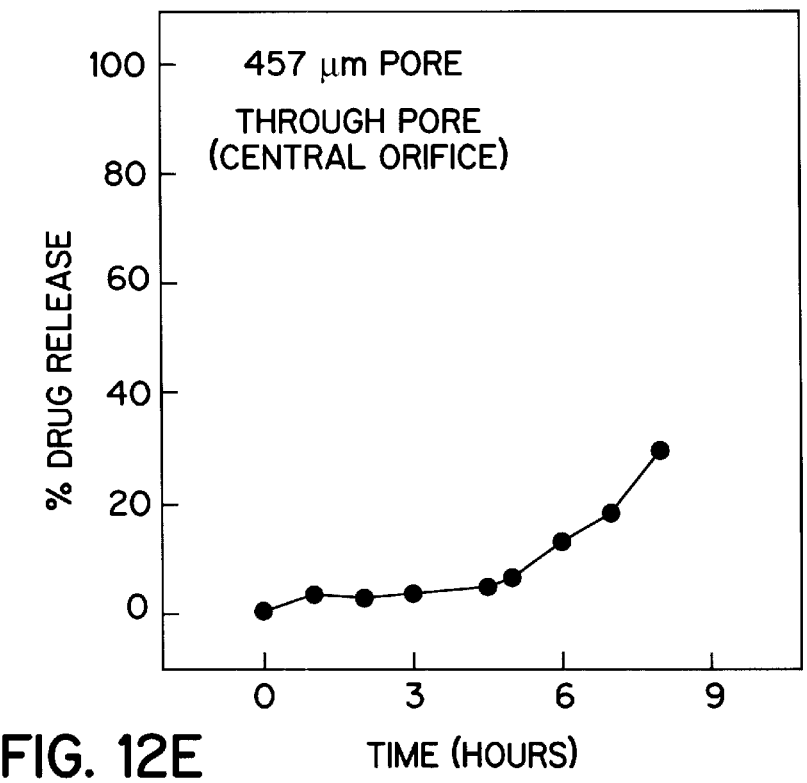
Figure 12F:
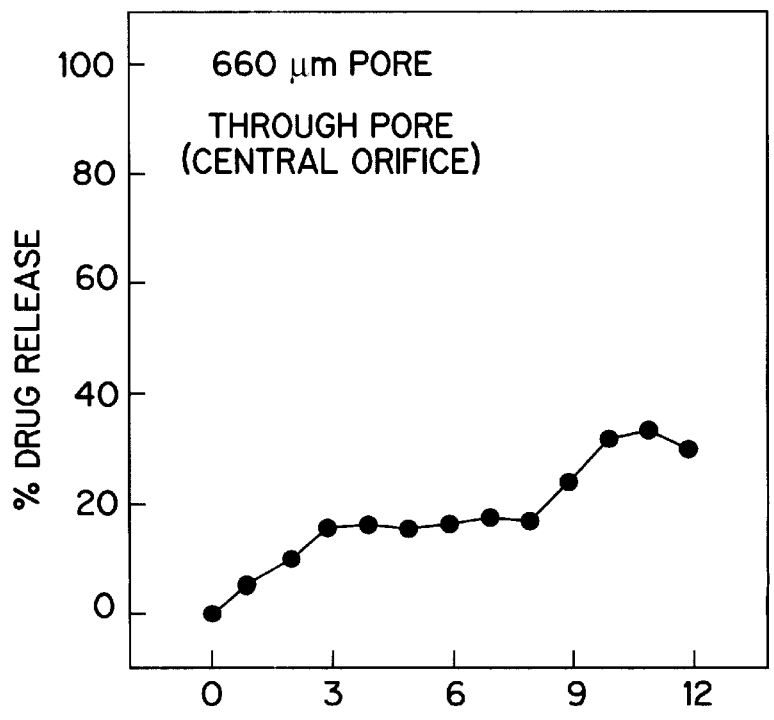
Figure 13A:
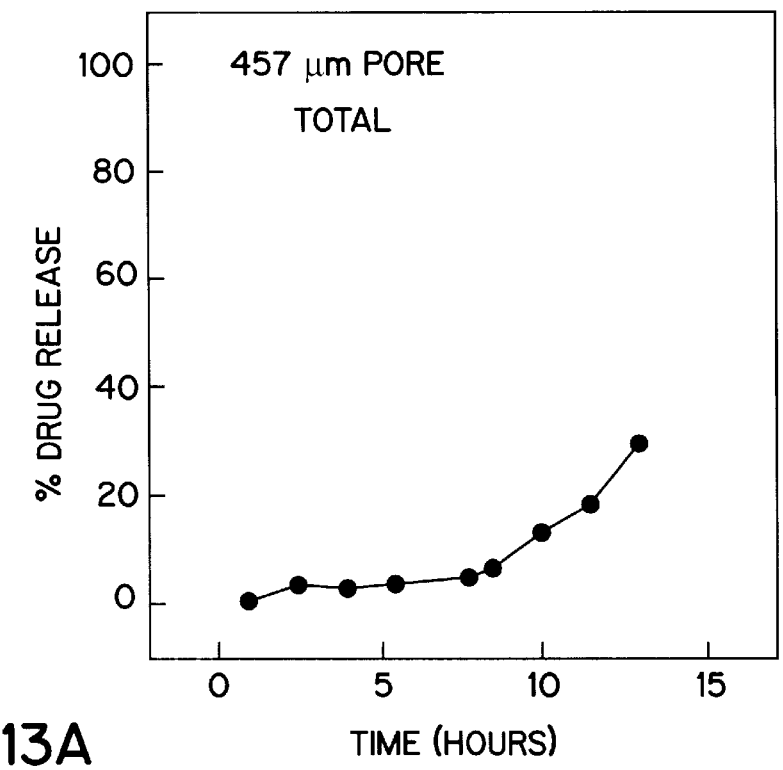
FIG. 13 shows the percent of drug released across the 375 mg shell and through the pore.
Figure 13B:
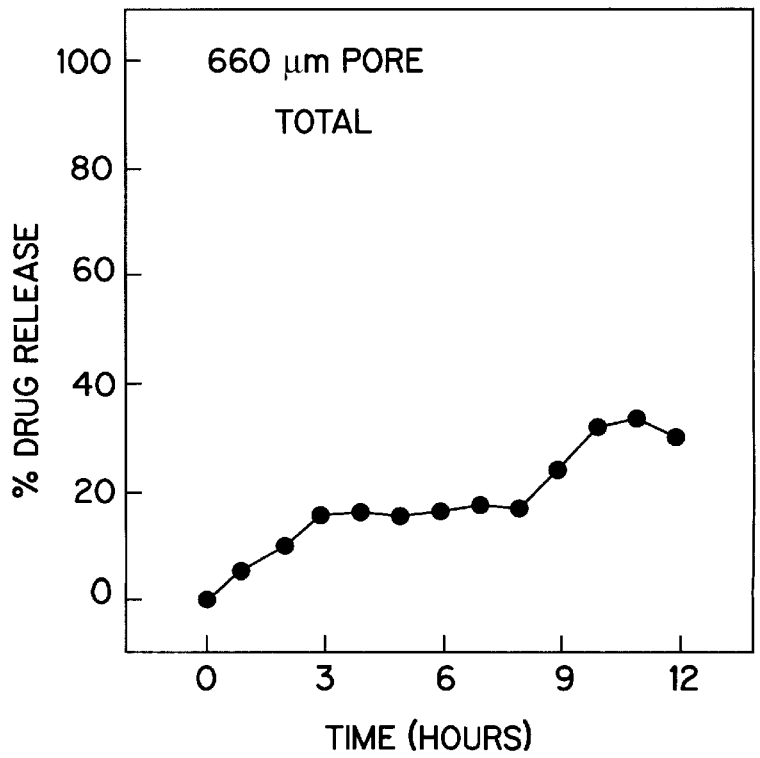
Figure 13C:
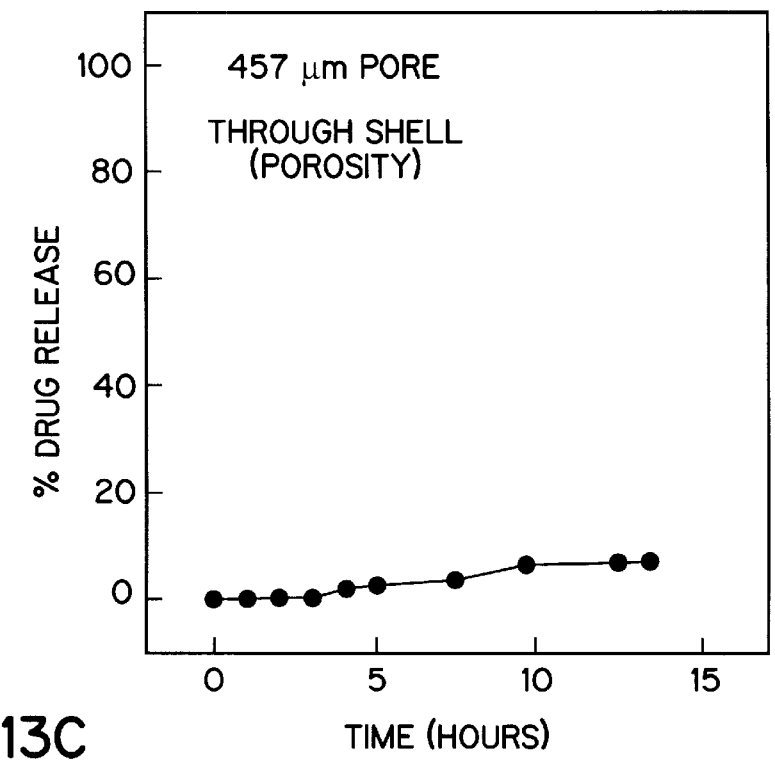
Figure 13D:
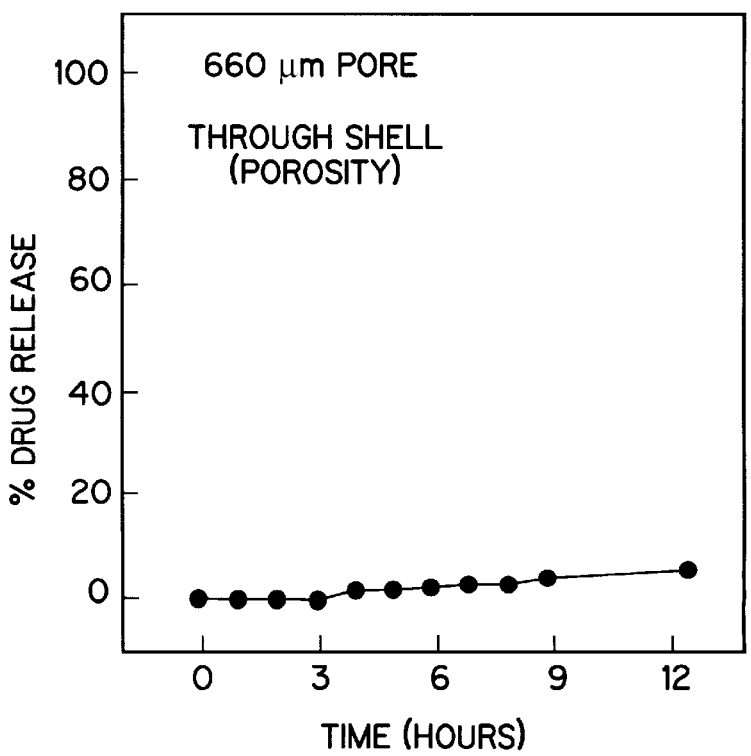
Figure 13E:
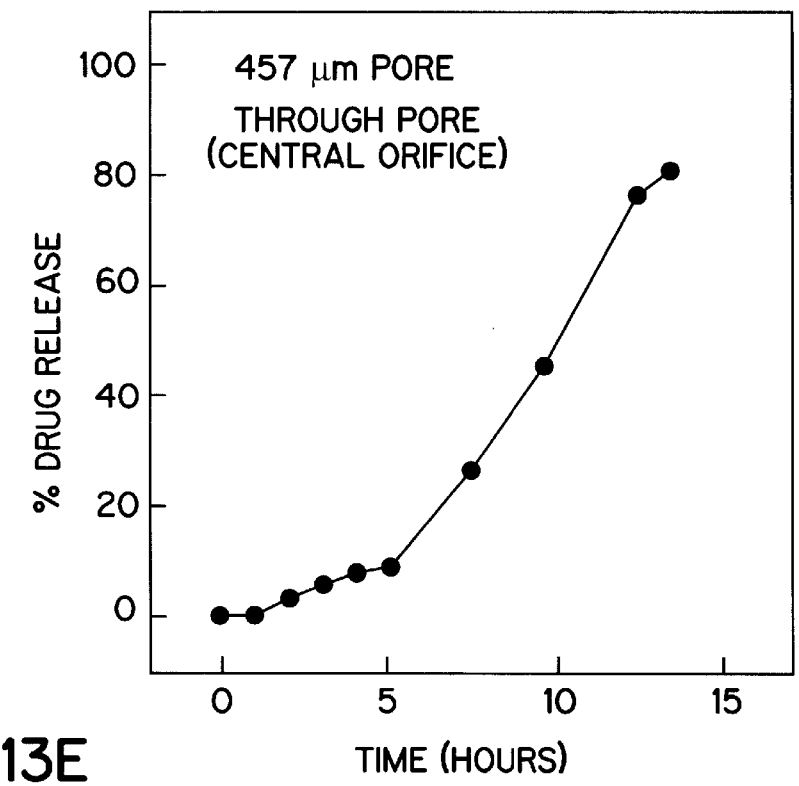
Figure 13F:
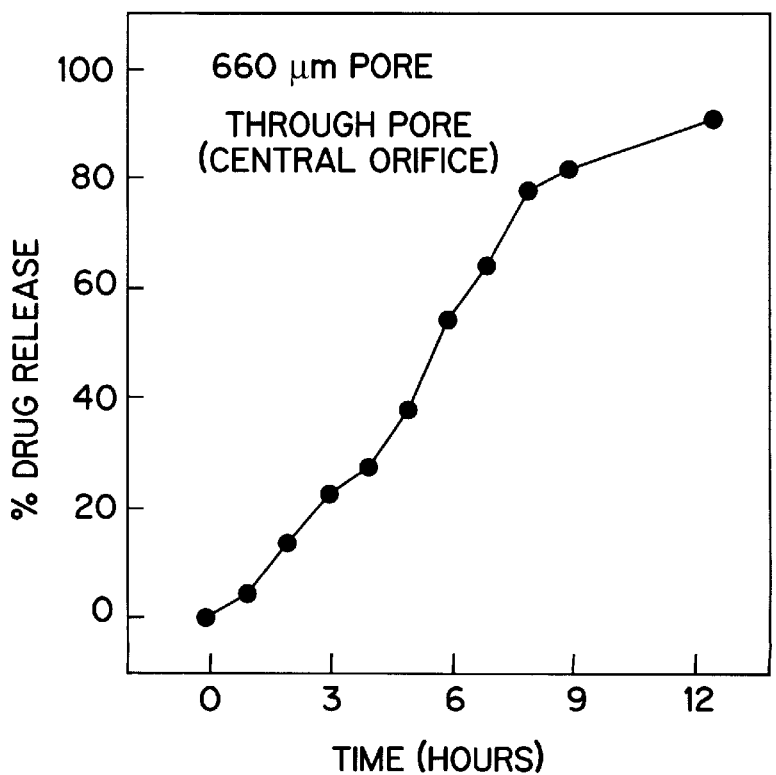

This reduction is more pronounced for pores 356 μm and larger. It is notable that the change in pore size makes a larger difference on drug release from thicker shells than from thinner shells. FIG. 11 shows the effect of shell amount on the time to release 75% of drug. An increase in shell amount slows the release of drug.

The shell is insoluble in water and for the release occurring across the shell, the drug has to first dissolve in the water imbibed by the system and then travel out according to the concentration gradient by diffusion. Increasing the size of the core (i.e., the cross-sectional diameter) from 7 mm to 9 mm decreases the time to release 75% of the drug. This may be explained by the fact that a larger core results in lesser thickness of the coat on the sides and an increased surface area of the core exposed to the dissolution medium imbibed by the system. Although the 9 mm core is thinner than the 7 mm core resulting in a thicker shell on the upper and lower surfaces of the system, this effect appears to be much less significant than the reduction of shell thickness on the sides.

FIGS. 12 and 13, show the percent of drug released across the shell and through the pore. The drug released across the shell represents drug released by the process of diffusion. The water imbibed into the system dissolves the drug in the core which then diffuses out. This is a two step process and therefore a lag time is seen. In case of drug release through the pore, diffusion is again the mechanism involved. However, the barrier in the form of the compression coated shell is absent. Depending on the size of the delivery orifice, the lag time for drug release through the pore may be long or short. For smaller pore sizes, the lag time may be quite prolonged and also the contribution to the total drug release may be very less.

In case of the system containing 300 mg shell, the predominant release route for the drug is diffusion across the shell. However, when the shell amount is increased to 375 mg, the predominant release route becomes the delivery orifice, accounting for almost all of the released drug.

The results of the fitting of the release data to various models are given in Tables 1 and 2. Overall, it can be seen that the S-N equation is the one that best fits the release profiles. The few deviations that are seen are for the 300 mg shell only. In general, the release profiles were sigmoidal with an initial lag or slow phase, a linear phase and finally tapering off or reaching a plateau.

In case of the 300 mg shell, the initial lag phase was too short, ranging from 0 to 1 hour, for all the pore sizes. On the other hand, the lag phase was too prolonged for the 425 mg shell system, ranging from 5 to 10 hours for the 9 mm core and about 5 hours for the 7 mm core, for all pore sizes. In addition, an increase in the pore size decreased the lag phase within this range.

The release of drug from the 7 mm core system was more gradual than the 9 mm core system and therefore the 7 mm core system was selected for further evaluation. Also, the 375 mg shell appears to be much more suited for controlled delivery applications due to its intermediate lag time and a gradual drug release profile. With regards to the size of the delivery orifice, sizes of 356 μm or more showed more pronounced effects on drug release profiles compared to the smaller or no pore systems. Therefore, the 356 μm and 660 μm sizes were utilized in further developmental studies. The next part of the study incorporating a hydrogel and a model drug appears as the second part of this report.

TABLE 1

Correlation coefficients from fitting to different models for 7 mm core.

| Pore Size (µm) | Shell Amt (mg) | Hig | H-C | S-N | S-L |
|---|---|---|---|---|---|
| 0 | 300 | 0.949 | 0.991 | 0.977 | 0.990 |
|  | 375 | 0.813 | 0.889 | 0.899 | 0.883 |
|  | 425 | 0.910 | 0.964 | 0.971 | 0.950 |
| 254 | 300 | 0.914 | 0.995 | 0.980 | 0.982 |
|  | 375 | 0.546 | 0.683 | 0.725 | 0.660 |
|  | 425 | 0.849 | 0.922 | 0.958 | 0.579 |
| 356 | 300 | 0.912 | 0.994 | 0.975 | 0.986 |
|  | 375 | 0.814 | 0.923 | 0.954 | 0.899 |
|  | 425 | 0.820 | 0.905 | 0.907 | 0.836 |
| 457 | 300 | 0.889 | 0.855 | 0.846 | 0.858 |
|  | 375 | 0.905 | 0.932 | 0.930 | 0.926 |
|  | 425 | 0.779 | 0.872 | 0.942 | 0.817 |
| 660 | 300 | 0.834 | 0.803 | 0.628 | 0.984 |
|  | 375 | 0.940 | 0.978 | 0.984 | 0.940 |
|  | 425 | 0.822 | 0.916 | 0.962 | 0.850 |
| 0 | 375[1] | 0.912 | 0.962 | 0.983 | 0.936 |
| 356 | 375[1] | 0.892 | 0.940 | 0.978 | 0.900 |
| 660 | 375[1] | 0.788 | 0.903 | 0.959 | 0.841 |

[1]Compressed to a hardness of 13.4 kp.

TABLE 2

Correlation coefficients from fitting to different models for 9 mm core.

| Pore Size (µm) | Shell Amt (mg) | Hig | H-C | S-N | S-L |
|---|---|---|---|---|---|
| 0 | 300 | 0.933 | 0.932 | 0.883 | 0.952 |
|  | 375 | 0.933 | 0.961 | 0.992 | 0.924 |
|  | 425 | 0.813 | 0.880 | 0.925 | 0.853 |
| 254 | 300 | 0.882 | 0.800 | 0.758 | 0.818 |
|  | 375 | 0.833 | 0.926 | 0.951 | 0.900 |
|  | 425 | 0.677 | 0.795 | 0.873 | 0.745 |
| 356 | 300 | 0.887 | 0.955 | 0.982 | 0.933 |
|  | 375 | 0.740 | 0.793 | 0.907 | 0.721 |
|  | 425 | 0.730 | 0.838 | 0.907 | 0.788 |
| 457 | 300 | 0.891 | 0.946 | 0.984 | 0.911 |
|  | 375 | 0.963 | 0.992 | 0.977 | 0.983 |
|  | 425 | 0.884 | 0.933 | 0.965 | 0.910 |
| 660 | 300 | 0.937 | 0.967 | 0.996 | 0.924 |
|  | 375 | 0.948 | 0.982 | 0.989 | 0.968 |
|  | 425 | 0.949 | 0.986 | 0.987 | 0.981 |

The first part deals with the effect of core size, shell amount and pore size, only, on drug release across the shell and through the pore, in absence of the hydrogel. The amount of shell and the size of the delivery orifice have been optimized and reported earlier. In this report, the addition of a hydrogel disk is described. The complete system has been finally evaluated using a model drug, chlorpheniramine maleate.

To overcome the problem of lag time for drug release from the system, the incorporation of an immediate release layer was proposed and evaluated. In this investigation, a second system incorporating an immediate release layer was also prepared and evaluated in vitro.

The goal is to deliver the drug at a controlled rate over a predetermined period of 8 or 14 hours for a 12 or 24 hours duration of effect.

Example 2
In Vitro Analysis of a Hydrogel Piston Pump

Materials and Methods

For the evaluation of the effect of hydrogel disk incorporation on drug release from the system, a water soluble marker, methylene blue was used. The final evaluation was done using a model drug, chlorpheniramine maleate. The formulation of the core tablets, hydrogel disk and the immediate release layer is as follows.

Methylene Blue Core Tablets 2.25 g of methylene blue (Fisher Scientific, Fairlawn, N.J.) and 20.25 g of lactose (Pfanstiehl Laboratories, Waukegon, Ill.) were mixed and kneaded with dropwise addition of distilled water (5 mL). The moist dough was passed through a 0.8 mm screen and allowed to dry for 20 hours at room temperature. The dried mixture was again screened through a 0.8 mm screen. Then 2.5 g of PEG 6000 (Matheson, Coleman and Bell Manufacturing Chemists, Norwood, Ohio) was blended into the mixture and the granules compressed into either 7 mm or 9 mm dia. biconvex tablets having a hardness of approximately 1 kp. The tablets (50 mg each) were compressed individually on a Carver Laboratory Press (Model C, Fred S. Carver, Inc., Menomonee Falls, Wis.).

Chlorpheniramine Maleate Core Tablets 6.25 g of chlorpheniramine maleate (City Chemical Corporation, New York, N.Y.) and 5.0 g of lactose (Pfanstiehl Laboratories, Waukegon, Ill.) were mixed and kneaded with dropwise addition of distilled water (2.5 mL). The moist dough was passed through a 0.8 mm screen and allowed to dry for 20 hours at room temperature. The dried mixture was again screened through a 0.8 mm screen. Then 1.25 g of PEG 6000 (Matheson, Coleman and Bell Manufacturing Chemists, Norwood, Ohio) was blended into the mixture and the granules compressed into 7 mm dia. biconvex tablets having a hardness of approximately 2.4 kp. The tablets (50 mg each) were compressed individually on a Carver Laboratory Press.

Agar Disks 1.44 g of agar (EM Science, Gibbstown, N.J.) was dissolved in 30 mL of distilled water with heating. 72 mg of PEG 400 (Matheson, Coleman and Bell Manufacturing Chemists, Norwood, Ohio) was added and the solution heated to the first bubble of boiling. While hot, it was poured into a glass petri dish (9 cm dia.) and allowed to cool for 5 hours. While it was still soft, disks of 7 mm diameter were cut out with a cork borer and allowed to air dry at room temperature for 24 hours. Additionally, the effect of placing a nylon disk between the hydrogel and the drug core was studied.

Chlorpheniramine Immediate Release Layer 125 mg of chlorpheniramine maleate was mixed with 5 mg of Aerosil® (Degussa, Inc., Teterboro, N.J.), and 2.37 g of Avicel® (FMC corporation, American Viscose Division, Marcus Hook, Pa.). The dry mixed powder was placed directly into the die cavity at time of compression.

Compression Coat Shell 1.35 mL of 10% Tween 80 (Hilltop Research, Inc., Miamisville, Ohio) and 1.14 mL of 10% glycerin (Fisher Scientific) were mixed. 15 g of Ethocel® 45 cps (Dow Chemical Company, Midland, Miss.) was spread on a foil tray and warmed to 60° C. The Tween 80/glycerin mixture was sprayed evenly, using a spray bottle, on the ethocel. This was then warmed to 60° C. for 1 to 2 hours and the drying completed overnight at room temperature.

The final product was prepared as follows. Half of the amount of the shell granules (375 mg) were placed into the die. The core tablet was then centered over it by hand. Finally, the remaining shell granules were added and the tablets compressed on a Carver Laboratory Press using flat faced punches, 13 mm dia., to an approximate hardness of 13.4 kp. The delivery orifices were made manually using the appropriate size drill bits (E & J Swiggart Co., Cincinnati, Ohio).

Double Layer System

The double layer tablets were prepared by the same procedure as the compression coat tablets with the exception that prior to placing the first layer of shell in the die, 100 mg of the immediate release layer was placed in it. The delivery orifice was drilled on the side of the tablet opposite to the initial phase.

The in vitro release profiles, from the delivery system, were studied in 900 mL of distilled water containing 0.02% Tween 80 and maintained at 37° C. The U.S.P. paddle dissolution method (United States Pharmacopeia, XXI Edition (1985), pp. 1243–1244) was used with the rotation speed of the paddles maintained at 100 rpm. Samples (3 mL) were withdrawn, with replacement, from the dissolution vessels and the methylene blue content was determined spectrophotometrically at 609 nm. Similarly, the chlorpheniramine maleate content was determined spectrophotometrically at 262 nm.

The in vitro release profiles were fitted to four different equations. The Higuchi equation (Hig) describes the % release vs (time)$^{1/2}$ profile. The Hixon-Crowell (H-C) equation relates $W_o^{1/3} - W_t^{1/3}$ to time, where, $W_o$ is the amount remaining to be released at time 0 and $W_t$ is the amount remaining to be released at time t. The Sigma Minus numeric (S-N) relationship is between numeric % remaining to be released and time whereas the Sigma Minus Semilog (S-L) is between log(% remaining to be released) and time.

Results and Discussion

Figure 14A:
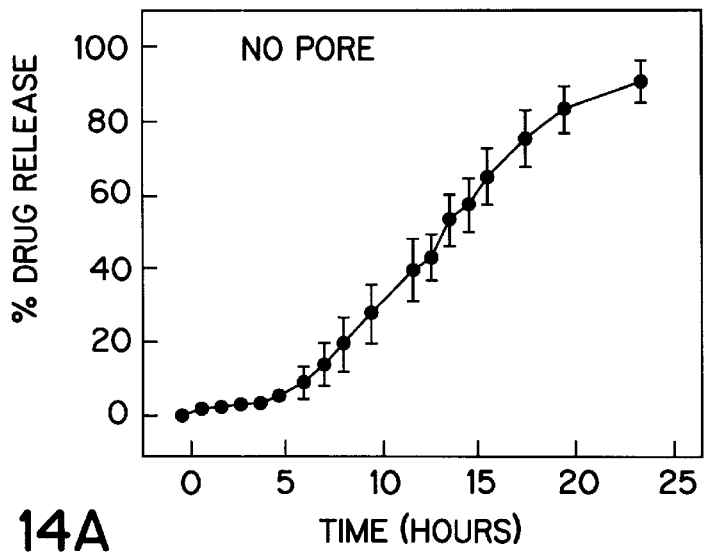
FIG. 14 depicts the in vitro release profile of methylene blue from the system in the absence of the swelling agent (hydrogel) disk.
Figure 14B:
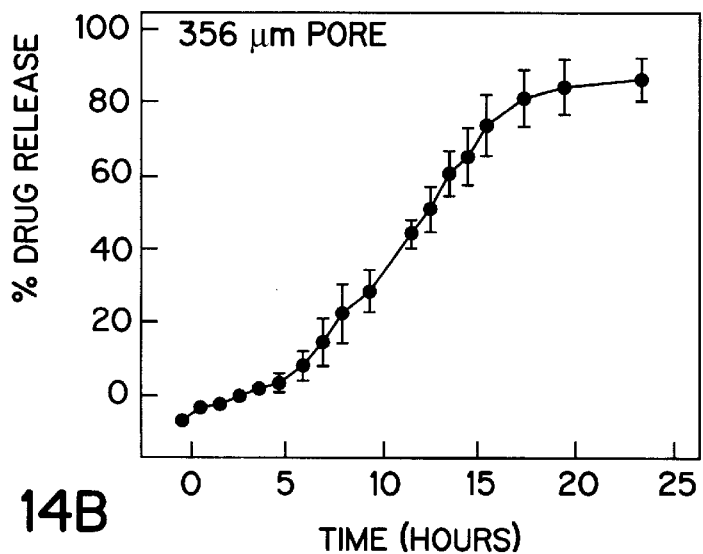
Figure 14C:
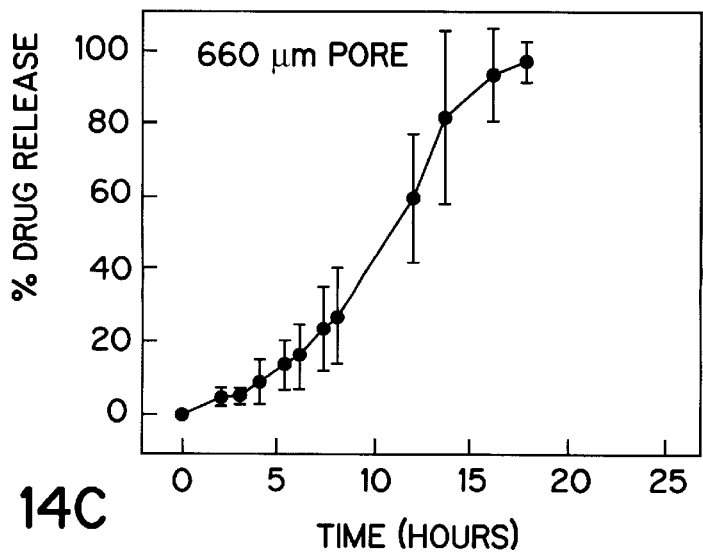
Figure 15A:
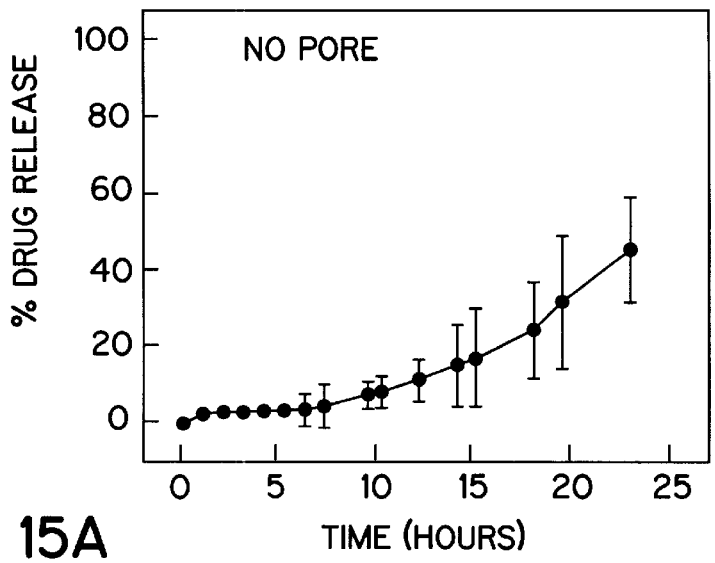
FIG. 15 depicts the in vitro release profile of methylene blue from the system in the presence of the swelling agent (hydrogel) disk.
Figure 15B:
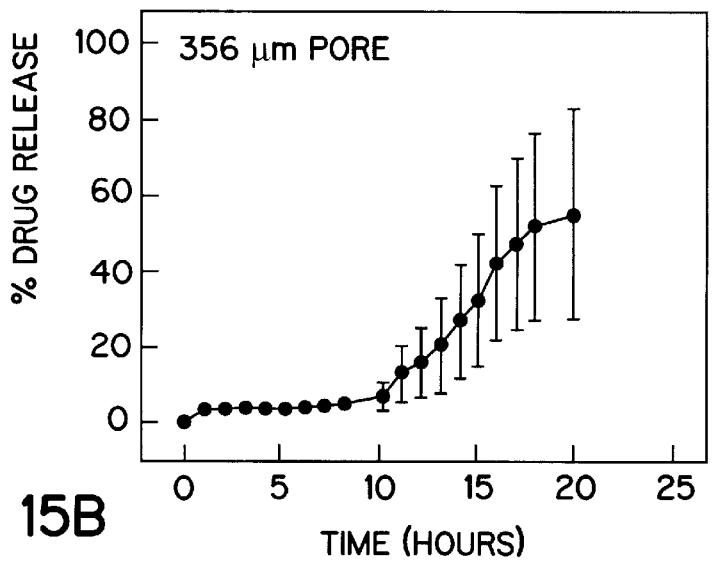
Figure 15C:
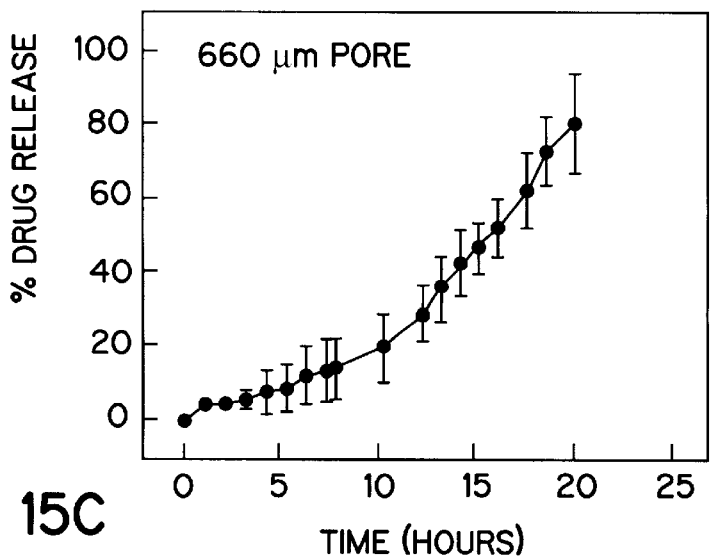
Figure 16A:
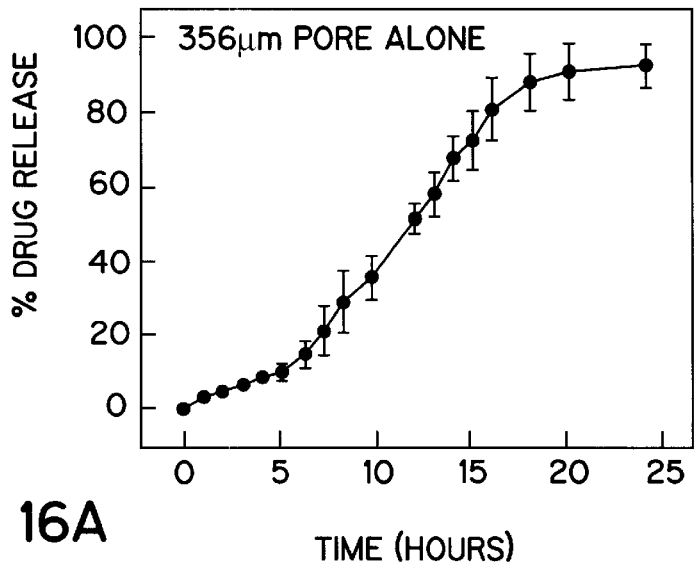
FIG. 16 depicts the release of drug from the device when a non-permeable nylon disk of the same diameter as the core is placed between the drug core and the swelling agent disk.
Figure 16B:
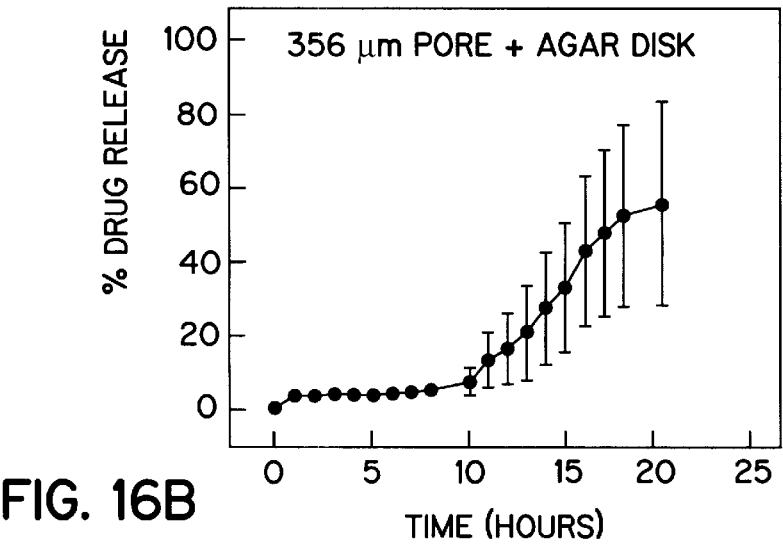
Figure 16C:
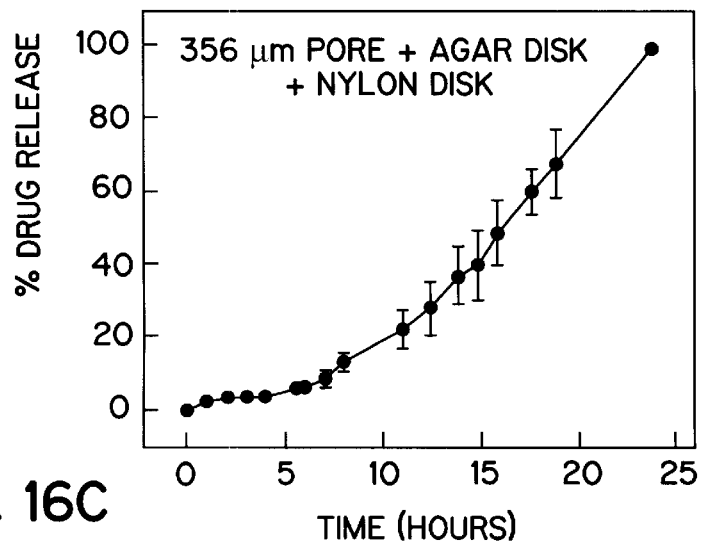

The in vitro release profile of methylene blue from the system in absence and in presence of the hydrogel disk is shown in FIGS. 14 and 15, respectively. Although it was anticipated that the presence of the swellable hydrogel would facilitate the drug release, this does not seem to be true. On the contrary, the release of the drug was slowed down from the system containing the hydrogel disk. A possible explanation for this could be that the water imbibed into the system is preferentially taken up by the hydrogel than by the drug core. This delay in the drug going into solution therefore delays its release. Secondly, an equilibrium within the shell could be created whereby the drug diffuses into the hydrogel and is therefore not available for release outside. This is borne out by the fact that the total release of drug is much lower in 24 hours from the system containing the hydrogel than the system without it. This is particularly true for the system not having a delivery orifice where the release of drug would be across the shell only.

To verify this hypothesis, we prepared a system in which we placed a non-permeable nylon disk of the same diameter as the core, between the drug core and the agar disk. As can be seen from FIG. 16, the release of drug is faster and much more uniform and complete in presence of the nylon disk.

The results of the fitting of the drug release profiles are shown in Table 3. It can be seen that the sigmoidal drug release profile seen is best fitted by the S-N model, in all cases studied.

In the next step, we incorporated a model drug, chlorpheniramine maleate in the system. The chlorpheniramine release profiles were similar to the release profiles from the corresponding systems containing methylene blue. In case of the chlorpheniramine system, the incorporation of the nylon disk between the drug core and the hydrogel, did not result in any significant improvement in the release profile and therefore, in the final dosage form, it was not incorporated.

Figure 17:
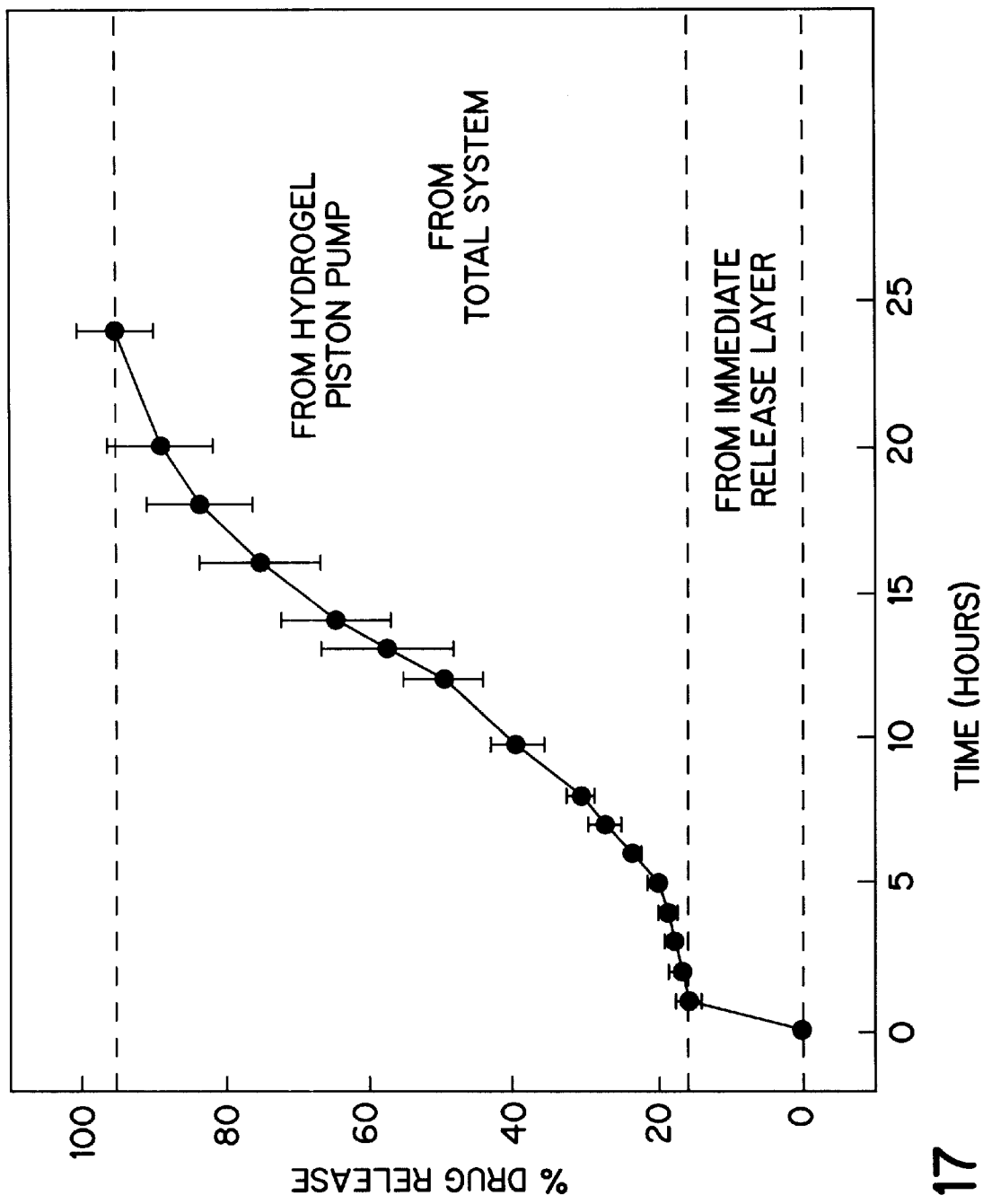
FIG. 17 depicts the in vitro release profile of the compression coated shell with a 356 μm delivery orifice and an immediate release layer containing an initial loading dose of the drug.

The final dosage form developed as a result of the study consisted of a 7 mm diameter core tablet and a 4.8% agar disk (serving as the piston 50) enclosed in a 375 mg compression coated shell with a 356 μm delivery orifice and an immediate release layer containing an initial loading dose of the drug. The in vitro release profile of this system is shown in FIG. 17.

Taking into consideration, the initial loading dose, the release profile approximates a zero order release pattern for about 20 hours. The results of the fitting of the release profiles from the different systems containing chlorpheniramine maleate, to the different models is given in Table 4. As expected, the S-N model is the one that best fits the release profile in all cases studied.

TABLE 3

Correlation coefficients from fitting to different models for the methylene blue system.

| Pore Size μm | Hig | H-C | S-N | S-L |
|---|---|---|---|---|
| 0 (−A) | 0.912 | 0.962 | 0.983 | 0.936 |
| 0 (+A) | 0.841 | 0.923 | 0.942 | 0.913 |
| 0 (+A + N) | 0.863 | 0.840 | 0.960 | 0.723 |
| 356 (−A) | 0.892 | 0.940 | 0.978 | 0.900 |
| 356 (+A) | 0.666 | 0.815 | 0.844 | 0.799 |
| 356 (+A + N) | 0.745 | 0.706 | 0.921 | 0.524 |
| 660 (−A) | 0.788 | 0.903 | 0.959 | 0.841 |
| 660 (+A) | 0.784 | 0.865 | 0.933 | 0.818 |

A = Agar Disk
N = Nylon Disk

TABLE 4

Correlation coefficients from fitting to different models for chlorpheniramine maleate system.

| Pore Size μm | Hig | H-C | S-N | S-L |
|---|---|---|---|---|
| 0 (+A) | 0.812 | 0.933 | 0.964 | 0.911 |
| 356 (+A) | 0.819 | 0.933 | 0.957 | 0.908 |
| 356 (+A + N) | 0.830 | 0.946 | 0.964 | 0.923 |
| DLT | 0.893 | 0.946 | 0.974 | 0.895 |

A = Agar Disk
N = Nylon Disk
DLT = Double Layer Tablet

Example 3

In Vivo Analysis of a Hydrogel Piston Pump in Humans

Materials and Methods

The hydrogel piston pump consists of a drug core and a hydrogel disk enclosed in a compression-coated shell of ethylcellulose. The shell contains a delivery orifice and coated disintegrant. The coated disintegrant provides the final burst effect to overcome the physiologic decrease in absorption. An immediate release layer is included to compensate for the lag time in delivery of the drug from the system.

The model drug selected was promethazine because it's pharmacokinetic parameters of relatively short half-life, low dose and short dosing interval, make it suitable for controlled release applications. The study was approved by the Institutional Review Board (IRB) of the University of Cincinnati. The delivery device of the present invention was evaluated in comparison with the commercially-available, immediate release product, PHENERGAN (25 mg).

The study was conducted in six healthy adults in a single dose, open label, randomized, two treatment, two period, cross-over design. All subjects were found to be in good health. The mean ± SD age was 24.83±2.86 y (range 22–30). The mean ±SD body weight and height were 63.33 ±9.46 kg (range 49–78) and 169.8±2.93 cm (range 167–174) respectively.

Each subject was assigned to one of the two treatment groups, immediate release formulation followed by the self-destructing device of the present invention (Group A) or the self-destructing device of the present invention followed by the immediate release formulation (Group B), by random. The treatment schedule was as shown in Table 5. Blood was collected at 0.25, 0.5, 0.75, 1, 1.5, 2, 3, 4, 5, 6, 8, 10, 12, 24, and 26 hours post dosing.

TABLE 5

Design of the in vivo human study.

| Subject | Period 1 | Period 2 |
| --- | --- | --- |
| PJ | A | B |
| YZ | A | B |
| PM | A | B |
| SR | B | A |
| AB | B | A |
| SN | B | A |

A: Reference product (Phenergan", 25 mg tablets)
B: Test product (PLIZ-HPP)

In addition to comparing the pharmacokinetic parameters from the two treatments, several measures of efficiency of controlled release were calculated which included Plateau Time (PT) which is the duration over which the blood levels remained above 75% of the observed maximum concentration (Cmax); the Half-Value Duration (HVD) which is the duration over which the blood levels remained above 50% of the Cmax; the Strength of Retardation ($R_{HVD}$) which is the ratio of the HVD for the present invention device to the HVD of the immediate release device; the Percent Peak-Trough Fluctuation Predicted (%PTFP); and the Percent Swing Predicted (%SWP).

Results

The pharmacokinetic parameters of promethazine determined for both formulations are given in Tables 6 and 7. As can be seen from the promethazine blood levels, there is a considerable prolongation in the time over which the blood levels are observed.

The pharmacokinetic parameters were subjected to ANOVA, to check for significant differences between the two formulations. The model used was:

$$y_{ijkl} = \mu + T_i + P_j + SQ_k + SU_{l(k)} + E_{ij(k)l}$$

where, $\mu$ is the overall mean; $T_i$ is the treatment effect (i=2);

$P_j$ is the period effect (j=2); $SQ_k$ is the sequence effect (k=2);

$Su_{l(k)}$ is the subject effect which is nested within the sequence (I=3); and $E_{ij(k)l}$ is the error term.

TABLE 6

Pharmacokinetic parameters of promethazine obtained using the RESID computer program, after administration of the immediate release tablet to six subjects.

| Parameter | PJ | YZ | PM | SR | AB | SN | Mean | S.D. |
| --- | --- | --- | --- | --- | --- | --- | --- | --- |
| $k_a$ [h$^{-1}$] | 0.386 | 0.174 | 0.161 | 0.261 | 0.237 | 0.102 | 0.220 | 0.099 |
| $t_{1/2}$ [h] | 1.794 | 3.974 | 4.294 | 2.658 | 2.926 | 6.791 | 3.740 | 1.749 |
| $k_a$ [h$^{-1}$] | 3.337 | 1.221 | 0.587 | 1.158 | 1.441 | 1.270 | 1.502 | 0.944 |
| $V_d$/F [L, kg$^{-1}$] | 14.84 | 17.90 | 21.97 | 15.22 | 25.23 | 17.80 | 18.83 | 4.04 |

TABLE 6-continued

Pharmacokinetic parameters of promethazine obtained using the RESID computer program, after administration of the immediate release tablet to six subjects.

| Parameter | PJ | YZ | PM | SR | AB | SN | Mean | S.D. |
| --- | --- | --- | --- | --- | --- | --- | --- | --- |
| $CL_{tot}$/F [mL, min$^{-1}$, kg$^{-1}$] | 95.56 | 52.04 | 59.19 | 68.15 | 99.61 | 30.28 | 67.13 | 26.51 |
| $AUC_{0-\infty}$[(ng, mL$^{-1}$), h] | 88.99 | 135.7 | 106.8 | 98.41 | 53.63 | 215.0 | 116.4 | 55.14 |
| $AUMC_{0-\infty}$[(ng, mL$^{-1}$), h$^{-1}$] | 257.0 | 889.2 | 843.3 | 462.4 | 203.6 | 2.276 | 831.9 | 758.8 |
| MRT [h] | 2.89 | 6.55 | 7.90 | 4.70 | 4.92 | 10.59 | 6.26 | 2.72 |

TABLE 7

Pharmacokinetic parameters of promethazine obtained using the AUC-RPP computer program ($k_a$ obtained from the RESID analysis of the data after administration of the immediate release tablet was used). after administration of the hydrogel piston pump (HPP) dosage form to six subjects.

| Parameter | PJ | YZ | PM | SR | AB | SN | Mean | S.D. |
| --- | --- | --- | --- | --- | --- | --- | --- | --- |
| $k_a$ [h$^{-1}$] | 0.386 | 0.174 | 0.161 | 0.261 | 0.237 | 0.102 | 0.220 | 0.099 |
| $t_{1/2}$ [h] | 1.794 | 3.974 | 4.294 | 2.658 | 2.926 | 6.791 | 3.740 | 1.749 |
| $k_a$ [h$^{-1}$] | 4.182 | 1.141 | 2.300 | 1.533 | 2.281 | 1.113 | 2.092 | 1.151 |
| $V_d$/F [L, kg$^{-1}$] | 8.94 | 8.31 | 20.67 | 12.82 | 19.05 | 13.26 | 13.84 | 5.09 |
| $CL_{tot}$/F [mL, min$^{-1}$, kg$^{-1}$] | 57.53 | 24.11 | 55.45 | 55.75 | 75.24 | 22.54 | 48.44 | 20.81 |
| $AUC_{0-\infty}$ [(ng, mL$^{-1}$), h] | 384.3 | 761.7 | 296.0 | 303.6 | 184.6 | 750.9 | 446.9 | 248.0 |
| $AUMC_{0-\infty}$ [(ng, mL$^{-1}$), h$^{-1}$] | 4.580 | 11.955 | 3.664 | 3.728 | 1.451 | 12.484 | 6.310 | 4.696 |
| MRT [h] | 11.92 | 15.69 | 12.38 | 12.28 | 7.86 | 16.63 | 12.79 | 3.12 |

With regard to Tables 6 and 7, the RESID computer program is described in detail in Ritschel, W. A., "RESID: A Curve-Fitting Program to Generate Pharmacokinetic Parameters", presented at the International Symposium on Clinical Pharmacokinetics at Salzgitter-Ringelheim, Jul. 20, 1975, and the AUC-RPP computer program is described in detail in Ritschel, W., "AUC-RPP: Basic Computer Program for Compartment Model Independent Pharmacokinetic Analysis", *Methods and Findings in Experimental and Clinical Pharmacology*, 1986, Vol. 8, pp. 633–640. The disclosure of each of these documents is incorporated herein in its entirety by reference.

Statistically significant treatment effect was seen for all the pharmacokinetic parameters of Vd, CL, AUC, AUMC and MRT, at the 5% level (p<0.05). In the case of Vd and CL, the subject effect was also found to be significant; that is, the differences between human subjects were statistically significant. The sequence in which the two formulations were administered did not show a significant effect, nor did the treatment period have any significant effect.

The pharmacokinetic parameters indicate that the two formulations result in significantly different pharmacokinetic profiles. This can be attributed not to a difference in the disposition of the drug in the body, which is not expected to change, but in the difference in the absorption of the drug. In the case of the modified release delivery system of the present invention (a self-destructing, hydrogel piston pump), the absorption of the drug occurs over a much longer period of time and the drug was not completely eliminated by the time the last sample was collected. The incomplete elimination coupled with the prolonged absorption phase can result in the observed differences in the pharmacokinetic parameters.

A comparison of the variances for the different parameters was made using the F test. In case of Vd, the variances were found to be equal but in all other cases, the variances were not found to be equal. This indicates that the statistical analysis is not entirely valid due to unequal variances. However, considering the small sample size and the type of study, it is not surprising. In future studies therefore, it would be necessary to have a larger sample size.

To assess the efficacy of the modified release system in achieving the desired therapeutic advantage, various parameters were calculated, as described above. These parameters are summarized in Tables 8 and 9. The plateau time (PT) was not found to be statistically significantly different for the two formulations. This may be explained by the fact that, just as in the immediate release tablet, there is an immediate release component in the hydrogel piston pump. This is expected to provide the initial blood levels of the drug and compensate for the lag time in the delivery from the main system. However, it was observed that this produced a peak in the blood level which was similar to the one after the immediate release tablet. Since the peak was high and not prolonged, the PT was found to be similar for both formulations.

TABLE 8

Plateau Time (PT) and Half Value Duration (HVD) for the immediate release tablet (IR) and hydrogel piston pump (HPP).

| | PT (h) | | HVD (h) | |
|---|---|---|---|---|
| Subject | IR | HPP | IR | HPP |
| PJ | 1.6 | 0.6 | 1.9 | 11.3 |
| YZ | 2.0 | 13.0 | 5.0 | 24.2 |
| PM | 4.2 | 3.9 | 7.8 | 8.0 |
| SR | 3.0 | 5.0 | 5.0 | 12.0 |
| AB | 2.5 | 2.2 | 4.2 | 7.8 |
| SM | 4.0 | 10.8 | 8.3 | 22.4 |
| Mean | 2.90 | 5.92 | 5.37 | 14.28 |
| S.D. | 1.05 | 4.92 | 2.37 | 7.21 |

TABLE 9

Corrected and uncorrected Percent Peak Trough Fluctuation Predicted (% PTFP) and Percent Swing Predicted (% SWP) for the immediate release tablet (IR) and hydrogel piston pump (HPP).

| | % PTFP | | | % SWP | | |
|---|---|---|---|---|---|---|
| Subject | IR (Uncor.) | IR (Cor.) | HPP | IR (Uncor.) | IR (Cor.) | HPP |
| PJ | 789.8 | 781.7 | 114.2 | 29,300 | 7,250 | 225.8 |
| YZ | 315.9 | 255.8 | 41.24 | 17,850 | 412.9 | 59.5 |
| PM | 238.4 | 173.3 | 127.4 | 10,610 | 257.0 | 209.5 |
| SR | 424.4 | 402.4 | 120.6 | 17,400 | 1,650 | 206.1 |
| AB | 429.1 | 384.3 | 256.3 | 9,570 | 779.1 | 2,190 |
| SN | 201.7 | 123.5 | 54.27 | 17,970 | 158.1 | 95.9 |
| Mean | 399.9 | 353.5 | 119.0 | 17,117 | 1,751 | 497.8 |
| S.D. | 212.6 | 237.3 | 76.4 | 7,058 | 2,748 | 831.8 |

With respect to the data presented in Table 9, "uncorrected" means the raw value as read, whereas "corrected" means the normalized value. Values were normalized by identifying the peak value of each subject as 100% (adjusted peak value), and subsequently expressing the corresponding trough value as a percentage of the adjusted peak value.

In contrast, the half-value duration (HVD), which is similar to the PT, but at half the peak height, was found to be marginally significantly different in the two treatment groups (p=0.0473). It becomes apparent that there is a significant prolongation in the time over which the blood levels are maintained above a certain concentration. The therapeutic concentrations for promethazine have not been determined and therefore it is not possible to compare the actual durations of action after administration of the two formulations.

A more meaningful parameter is the percent peak-trough fluctuation predicted (%PTFP) and the percent swing predicted (%SWP). Both these parameters provide a measure of the expected fluctuations in the blood concentrations at steady state, assuming linear pharmacokinetics. In effect, the lower the fluctuations, the more efficacious the formulation. This is especially true for modified release formulations.

The %PTFP value is lower after administration of the modified release system. The difference is found to be statistically significant. The corrected %PTFP values are also lower than the immediate release product, although not significantly lower at p=0.05. The difference is however, significant at p=0.1.

The above description is for the purpose of teaching the person of ordinary skill in the art how to practice the present invention and it is not intended to detail all those obvious modifications and variations of it which will become apparent to the skilled worker upon reading the description. It is intended, however, that all such obvious modifications and variations be included within the scope of the present invention and by the following claims.

What is claimed:

1. An oral tablet for delivering a beneficial agent to a mammal, comprising:
   a core compartment having a beneficial agent; and
   a unitary self-destructing shell surrounding the core compartment, the self-destructing shell comprising a plurality of disintegrant particles dispersed within a semipermeable matrix.

2. The tablet of claim 1 wherein the core compartment further comprises means for delivering the beneficial agent from the tablet.

3. The tablet of claim 1 wherein the self-destructing shell comprises at least one disintegrant within a matrix.

4. The tablet of claim 3 wherein the disintegrant comprises a core surrounded by a disintegrant delay jacket, the core including a swelling agent.

5. The tablet of claim 4 wherein the swelling agent is selected from the group consisting of an insoluble polysaccharide, a hydrogel, a swellable, hydrophilic polymer, a water insoluble copolymer of maleic anhydride, a water swellable polymer of an N-vinyl lactam, a polymer which forms a hydrogel upon contact with an imbibed fluid, and combinations thereof.

6. The tablet of claim 5 wherein the insoluble polysaccharide is selected from the group consisting of starch, cellulose, and combinations thereof.

7. The tablet of claim 5 wherein the hydrogel is selected from the group consisting of polyethylene glycol, hydroxypropyl methylcellulose, hydroxyethyl cellulose, and combinations thereof.

8. The tablet of claim 5 wherein the swellable, hydrophilic polymer is selected from the group consisting of poly (hydroxyalkylmethacrylate, poly(vinylpyrrolidone, polyelectrolyte complexes, poly(vinyl alcohol, methyl cellulose, cross-linked agar, carboxymethyl cellulose, and combinations thereof.

9. The tablet of claim 5 wherein the water insoluble copolymer of maleic anhydride includes a monomer selected from the group consisting of styrene, ethylene, propylene, butylene, isobutylene, and combinations thereof.

10. The tablet of claim 5 wherein the polymer which forms a hydrogel upon contact with an imbibed fluid is selected from the group consisting of an acidic carboxy polymer, a metal salt of an acidic carboxy polymer, a polyacrylamide, a cross-linked, water-swellable, indine-maleic anhydride polymer, a polyacrylic acid, a metal salt of a polyacrylic acid, a polyethylene oxide polymer, a starch graft copolymer, an acrylate polymer; a diester cross-linked polyglucan, and combinations thereof.

11. The tablet of claim 4 wherein the disintegrant delay jacket comprises a component selected from the group consisting of a binder, an osmotic agent, a tablet lubricant, and combinations thereof.

12. The tablet of claim 3 wherein the matrix includes a material selected from the group consisting of cellulose acetate, ethylcellulose, a polymethacrylic acid ester, an acrylic acid ester/methacrylic acid copolymer with at least one quarternary ammonium group, cellulose triacetate, agar acetate, amylose triacetate, beta glucan acetate, beta glucan triacetate, cellulose acetate ethyl carbamate, cellulose acetate phthalate, cellulose acetate methyl carbamate, cellulose acetate succinate, cellulose acetate dimethylaminoacetate, cellulose acetate ethyl carbonate, cellulose acetate methyl sulfonate, cellulose acetate butyl sulfonate, a cellulose ether, cellulose acetate propionate, a polyvinyl methyl ether polymer, cellulose acetate laurate, methyl cellulose, cellulose acetate p-toluene sulfonate, triacetate of locust bean gum, cellulose acetate with acetylated hydroxyethyl cellulose, hydroxylated ethylenevinylacetate, a polymeric epoxide, an alkylene oxide-alkyl glycidyl ether, a polyurethane, polyglycolic acid, and combinations thereof.

13. The tablet of claim 3 wherein the matrix includes a material selected from the group consisting of cellulose acetate, ethylcellulose, a polymethacrylic acid ester, an acrylic acid ester/methacrylic acid copolymer with at least one quarternary ammonium group, and combinations thereof.

14. The tablet of claim 1 wherein the self-destructing shell comprises at least one aqueously dispersible, pharmaceutically acceptable, polymeric compound.

15. The tablet of claim 14 wherein the aqueously dispersible, pharmaceutically acceptable, polymeric compound is selected from the group consisting of a methacrylic ester copolymer, poly(ethyl acrylate, methyl methacrylate), poly(ethyl acrylate, methyl methacrylate, trimethylammonioethyl methacrylate chloride), a polymethyl methacrylate-methacrylic acid copolymer, cellulose acetate, ethylcellulose, cellulose acetate phthalate, hydroxypropyl methylcellulose phthalate, and combinations thereof.

16. The tablet of claim 1 wherein the beneficial agent formulation further includes an additional agent, the additional agent selected from the group consisting of an osmotic agent, a lubricant, a glidant, a wetting agent, a viscosity-modulating vehicle, a surfactant, a binder, a filler, a suspending agent, a thickening agent, a pharmaceutically acceptable carrier, and combinations thereof.

17. The tablet of claim 1 wherein the beneficial agent formulation comprises from about 5 nanograms to about 20 grams of the first beneficial agent.

18. The tablet of claim 1 wherein the first beneficial agent is selected from the group consisting of a protein, a peptide, an antiasthmatic, an antianginal, a corticosteroid, a 5-lipoxygenase inhibitor, an antihypertensive, a leukotriene B4 receptor antagonist, and combinations thereof.

19. The tablet of claim 1 wherein the first beneficial agent is selected from the group consisting of theophylline, IGF-l, PTH (1–34), TGF alpha, TGF beta 1, TGF beta 2, TGF beta 3, IFN alpha, hybrid IFN alpha, IFN gamma, hirudin, heparin, calcitonin, 5-aminosalicylic acid, N-hydroxy-N-((6-phenoxy-2H-1-benzopyran-3-yl)methyl)-urea, 4-[5-[4-(aminoiminomethyl)phenoxy]pentoxy]-3-methoxy-N,N-bis (1-methylethyl)benzamide (Z)-2-butenedioate, N-[2-[[2-[[4-(4-fluorophenyl)phenyl]methyl]-1,2,3,4-tetrahydro-1-oxo-6-isoquinolinyl]oxy]ethyl]-N-hydroxyurea, 1-(1-benzo[b]thien-2-ylethyl)-1-hydroxyurea, 5-[2-(2-carboxyethyl)-3-[6-(para-methoxyphenyl)-5E-hexenyl]oxyphenoxy]valeric acid, beclomethasone dipropionate, betamethasone-17-valerate, prednisolone metasulfobenzoate, tixocortol pivalate, budesonide, fluticasone, metoprolol, a pharmaceutically acceptable salt thereof, and combinations thereof.

20. The tablet of claim 1 wherein the core compartment further comprises an osmotic agent.

21. The tablet of claim 1 wherein the core compartment further comprises an excipient selected from the group consisting of a binder, a hygroscopic suspending agent, a hygroscopic thickening agent, a tablet lubricant, and combinations thereof.

22. The tablet of claim 1 further including a second beneficial agent, the second beneficial agent positioned exterior to the self-destructing shell.

23. The tablet of claim 22 further comprising an enteric coating.

24. The tablet of claim 23 wherein the enteric coating is selected from the group consisting of cellulose acetate phthalate NF, hydroxypropyl methylcellulose phthalate NF, polyvinyl acetate phthalate NF, methacrylic acid copolymer NF, and combinations thereof.

25. The tablet of claim 23 wherein the second beneficial agent is positioned between the self-destructing shell and the enteric coating.

26. The tablet of claim 23 wherein the enteric coating is positioned between the self-destructing shell and the second beneficial agent.

27. The tablet of claim 2 wherein the self-destructing shell further comprises an exit means.

28. The tablet of claim 27 wherein the exit means includes a release orifice.

29. The tablet of claim 28 wherein the release orifice has a cross-sectional diameter between about 0.05 mm and about 1.5 mm.

30. The tablet of claim 2 wherein the means for delivering the beneficial agent formulation from the delivery system includes a push means.

31. The tablet of claim 30 wherein the push means includes an osmopolymer.

32. The tablet of claim 31 wherein the osmopolymer is selected from the group consisting of an insoluble polysaccharide, a hydrogel, a swellable, hydrophilic polymer, a water insoluble copolymer of maleic anhydride, a water swellable polymer of an N-vinyl lactam, a polymer which forms a hydrogel upon contact with an imbibed fluid, and combinations thereof.

33. The tablet of claim 32 wherein the insoluble polysaccharide is selected from the group consisting of starch, cellulose, and combinations thereof.

34. The tablet of claim 32 wherein the hydrogel is selected from the group consisting of polyethylene glycol, hydroxypropyl methylcellulose, hydroxyethyl cellulose, and combinations thereof.

35. The tablet of claim 32 wherein the swellable, hydrophilic polymer is selected from the group consisting of poly(hydroxyalkylmethacrylate, poly(vinylpyrrolidone, polyelectrolyte complexes, poly(vinyl alcohol, methyl cellulose, cross-linked agar, carboxymethyl cellulose, and combinations thereof.

36. The tablet of claim 32 wherein the water insoluble copolymer of maleic anhydride includes a monomer selected from the group consisting of styrene, ethylene, propylene, butylene, isobutylene, and combinations thereof.

37. The tablet of claim 32 wherein the polymer which forms a hydrogel upon contact with an imbibed fluid is selected from the group consisting of an acidic carboxy polymer, a metal salt of an acidic carboxy polymer, a polyacrylamide, a cross-linked, water-swellable, indine-maleic anhydride polymer, a polyacrylic acid, a metal salt of a polyacrylic acid, a polyethylene oxide polymer, a starch graft copolymer, an acrylate polymer; a diester cross-linked polyglucan, and combinations thereof.

38. The tablet of claim 31 wherein a diaphragm is interposed between the osmopolymer and the beneficial agent formulation.

39. The tablet of claim 31 wherein the push means further comprises an osmagent.

40. The tablet of claim 39 wherein the osmagent is selected from the group consisting of an inorganic salt, a salt of an organic acid, an organic acid, a carbohydrate, a water-soluble amino acid, magnesium sulfate, magnesium carbonate, urea, saccharin, sodium saccharin, glycerin, hexylene glycol, polyethylene glycol, propylene glycol, and combinations thereof.

41. The tablet of claim 40 wherein the inorganic salt is selected from the group consisting of sodium chloride, potassium chloride, magnesium chloride, sodium hydrogen phosphate, potassium hydrogen phosphate, dihydrogen phosphate, and combinations thereof.

42. The tablet of claim 40 wherein the salt of the organic acid is selected from the group consisting of sodium alginate, sodium ascorbate, sodium benzoate, sodium citrate, edetate disodium, sodium fumarate, sodium acetate, potassium acetate, magnesium succinate, and combinations thereof.

43. The tablet of claim 40 wherein the organic acid is selected from the group consisting of alginic acid, ascorbic acid, citric acid, edetic acid, malic acid, sorbic acid, and combinations thereof.

44. The tablet of claim 40 wherein the carbohydrate is selected from the group consisiting of a dextrate, sorbitol, xylitol, maltitol, mannitol, arabinose, ribose, xylose, glucose, dextrose, fructose, galactose, mannose, sucrose, maltose, lactose, raffinose, and combinations thereof.

45. The tablet of claim 40 wherein the water-soluble amino acid is selected from the group consisting of glycine, leucine, alanine, methionine, and combinations thereof.

46. A method of delivering a beneficial agent to a mammal in need thereof, comprising the step of orally administering the tablet of claim 1 to the mammal.

47. A method of delivering a colonically-active or colonically-absorable beneficial agent to the colon of a mammal in need thereof, comprising the step of orally administering the tablet of claim 1 to the mammal.

48. A method of delivering a beneficial agent to a mammal in need thereof, comprising the step of orally administering the tablet of claim 2 to the mammal.

49. A method of delivering a beneficial agent to the lower portion of the small intestine of a mammal in need thereof, comprising the step of orally administering the tablet of claim 3 to the mammal.

50. A method of delivering a beneficial agent to the lower portion of the small intestine of a mammal in need thereof, comprising the step of orally administering the tablet of claim 15 to the mammal.

51. A method of delivering a beneficial agent to the lower portion of the small intestine of a mammal in need thereof, comprising the step of orally administering the tablet of claim 31 to the mammal.

52. A method of making an oral tablet for delivering a beneficial agent to a mammal, comprising the steps of:
   forming a core compartment having a beneficial agent; and
   surrounding the core compartment with a unitary self-destructing shell, the self-destructing shell comprising a plurality of disintegrant particles dispersed within a semipermeable matrix.

53. The method of claim 52 wherein each of the disintegrant particles comprises a core and a disintegrant delay jacket, the core including a swelling agent, and the disintegrant delay jacket surrounding the core.

54. The method of making an oral tablet for delivering a beneficial agent to a mammal, comprising the steps of:
   forming a core compartment including a first end wall, an oppositely disposed second end wall, a sidewall between the first and second end walls, a diaphragm having a first side and a second side, a beneficial agent positioned on one of the first and second sides, and a push means positioned on the other one of first and second sides, the diaphragm constructed and arranged to be slideble within the core compartment; and
   surrounding the core compartment with a unitary shell.

55. The method of claim 54 further including the step of positioning an external delay jacket exterior to the unitary shell.

56. The method of claim 54 wherein the unitary shell comprises a self-destructing shell having a plurality of disintegrant particles dispersed within a semi-permeable matrix.

57. The method of claim 56 further including the step of positioning an enteric coating exterior to the self-destructing shell.

58. The method of claim 57 further including the step of positioning a second beneficial agent exterior to the core compartment.

59. The method of claim 58 wherein the second beneficial agent is positioned between the self-destructing shell and the enteric coating.

60. The method of claim 58 wherein the second beneficial agent is positioned exterior to the enteric coating.

61. The method of claim 54 wherein the unitary shell is semi-permeable and includes an exit means.

62. The method of claim 54 wherein the push means includes an osmopolymer.

63. The method of claim 62 wherein the osmopolymer includes a dry hydrogel-forming powder.

64. The method of claim 58 further including the step of positioning an external delay jacket exterior to the self-destructing shell, the external delay jacket being water-soluble, permeable to the first and second beneficial agents, and comprising a component selected from the group consisting of a binder, an osmotic agent, a lubricant, and combinations thereof.

65. The oral tablet of claim 1 wherein the self-destructing shell is constructed and arranged to begin to erode by the time the oral tablet reaches the environment of use.

66. The oral tablet of claim 1 wherein the self-destructing shell is constructed and arranged to begin to erode before the oral tablet reaches the environment of use.

67. An oral tablet for delivering a beneficial agent to a mammal, comprising:
   a core compartment; and a unitary shell surrounding the core compartment, the core compartment including a first end wall, an oppositely disposed second end wall, and a sidewall between the first and second end walls, the core compartment further including a diaphragm having a first side and a second side, a beneficial agent positioned on one of the first and second sides, and a push means positioned on the other one of the first and second sides, the diaphragm constructed and arranged to be slideable within the core compartment.

* * * * *

UNITED STATES PATENT AND TRADEMARK OFFICE
CERTIFICATE OF CORRECTION

PATENT NO. : 6,365,185 B1
DATED : April 2, 2002
INVENTOR(S) : Wolfgang A. Ritschel et al.

It is certified that error appears in the above-identified patent and that said Letters Patent is hereby corrected as shown below:

Column 1,
Line 16, "tablets which are time-controlled controlled to" should read -- tablets which are time-controlled to --.
Line 66, "shell of the device self-destructs destructs thus" should read -- shell of the device self-destructs thus --.

Column 3,
Line 28, ""Delivery System": and filed on Mar. 26, 1998" should read -- "Delivery System" and filed on Mar. 26, 1998 --.

Column 8,
Line 16, "sodium tetraborate, sodium carbonate sodium hydrogen carbonate, and" should read -- sodium tetraborate, sodium carbonate, sodium hydrogen carbonate, and --.

Column 10,
Line 18, "poly(1,4-anhydro-beta-Dmannuroni acid);" should read -- poly(1,4-anhydro-beta-D-mannuroni acid); --.

Column 12,
Line 26, "As shown in Fig. 6, in an alternative embodiment, of wall 12 may comprise a" should read -- As shown in Fig. 6, in an alternative embodiment, wall 12 may comprise a --.

Column 15,
Line 6, "diester cross-liked linked polyglucan, and" should read -- diester cross-linked polyglucan, and --.
Line 17, "property of these hydro-gels is that it swells in the presence" should read -- property of these hydro-gels is that they swell in the presence of --.

Column 16,
Line 36, "Handbook of common Polymers; by Roff and Scott, published by" should read -- Handbook of Common Polymers by Roff and Scott, published by --.

Column 21,
Line 1, "Determination of Shell Thickness and Pore size Materials and Methods" should read
--      Determination of Shell Thickness and Pore Size Materials and Methods --.

UNITED STATES PATENT AND TRADEMARK OFFICE
CERTIFICATE OF CORRECTION

PATENT NO. : 6,365,185 B1
DATED : April 2, 2002
INVENTOR(S) : Wolfgang A. Ritschel et al.

It is certified that error appears in the above-identified patent and that said Letters Patent is hereby corrected as shown below:

Column 21 cont'd,
Line 29, "Midland, Miss." should read -- Midland, Mich. --.

Column 24,
Line 54, "Midland, Miss." should read -- Midland, Mich. --.

Column 27,
Line 54, "$Su_{1(k)}$ is the subject effect which is nested within the sequence (I-3); and" should read -- $Su_{1(k)}$ is the subject effect which is nested within the sequence (1=3); and --.

Column 28,
Line 8, "68.15" should read -- 66.15 --.
Line 12, "$h^{-1}$" should read -- $h^2$ --.
Line 12, "203.6" should read -- 263.6 --.
Line 34, "4.580" should read -- 4,580 --.
Line 34, "11.955" should read -- 11,955 --.
Line 34, "3.664" should read -- 3,664 --.
Line 34, "3.728" should read -- 3,728 --.
Line 34, "1.451" should read -- 1,451 --.
Line 34, "12.484" should read -- 12,484 --.
Line 34, "6.310" should read -- 6,310 --.
Line 34, "4.696" should read -- 4,696 --.
Line 37, "$h^{-1}$" should read -- $h^2$ --.
Line 54, "($p<0.05$)" should read -- ($p\leq0.05$) --.

Column 29,
Line 37, "2.5" should read -- 2.6 --.

Column 30,
Lines 60-65, "The tablet of claim 5 wherein the swellable, hydrophilic polymer is selected from the group consisting of poly(hydroxyalkylmethacrylate, poly(vinylpyrrolidone, polyelectrolyte complexes, poly(vinyl alcohol, methyl cellulose, cross-linked agar, carboxymethyl cellulose, and combinations thereof." should read -- The tablet of claim 5 wherein the swellable, hydrophilic polymer is selected from the group consisting of poly(hydroxyalkylmethacrylate), poly(vinylpyrrolidone), polyelectrolyte complexes, poly(vinyl alcohol), methyl cellulose, cross-linked agar, carboxymethyl cellulose, and combinations thereof. --.

UNITED STATES PATENT AND TRADEMARK OFFICE
CERTIFICATE OF CORRECTION

PATENT NO. : 6,365,185 B1
DATED : April 2, 2002
INVENTOR(S) : Wolfgang A. Ritschel et al.

It is certified that error appears in the above-identified patent and that said Letters Patent is hereby corrected as shown below:

<u>Column 32, lines 64-67 and Column 33, lines 1 and 2,</u>
"The tablet of claim 32 wherein the swellable, hydrophilic polymer is selected from the group consisting of poly(hdyroxyalkylmethacrylate, poly(vinylpyrrolidone, polyelectrolyte complexes, poly(vinyl alcohol, methyl cellulose, cross-linked agar, carboxymethyl cellulose, and combinations thereof." should read
-- The tablet of claim 32 wherein the swellable, hydrophilic polymer is selected from the group consisting of poly(hydroxyalkylmethacrylate), poly(vinylpyrrolidone), polyelectrolyte complexes, poly(vinyl alcohol), methyl cellulose, cross-linked agar, carboxymethyl cellulose, and combinations thereof. --.

Signed and Sealed this

Eighth Day of October, 2002

*Attest:*

JAMES E. ROGAN
*Director of the United States Patent and Trademark Office*

*Attesting Officer*